United States Patent
Eiseman

(12) 
(10) Patent No.: US 6,354,297 B1
(45) Date of Patent: Mar. 12, 2002

(54) METHOD AND DEVICE FOR DESTROYING FAT CELLS BY INDUCTION OF PROGRAMMED CELL DEATH

(75) Inventor: Ben Eiseman, Englewood, CO (US)

(73) Assignee: The Uniformed Services University of the Health Sciences, Bethesda, MD (US)

(*) Notice: Subject to any disclaimer, the term of this patent is extended or adjusted under 35 U.S.C. 154(b) by 0 days.

(21) Appl. No.: 09/184,773

(22) Filed: Nov. 2, 1998

Related U.S. Application Data

(60) Provisional application No. 60/082,036, filed on Apr. 16, 1998.

(51) Int. Cl.$^7$ ................................................ A61B 19/00
(52) U.S. Cl. .................................................... 128/898
(58) Field of Search .............................. 128/898; 607/1

(56) References Cited

U.S. PATENT DOCUMENTS

| | | | | |
|---|---|---|---|---|
| 4,684,623 A | * | 8/1987 | Larrick et al. ................. | 514/12 |
| 5,219,579 A | * | 6/1993 | Tisdale et al. ............... | 424/573 |
| 5,484,778 A | | 1/1996 | Kenney et al. ............... | 514/63 |
| 5,527,273 A | | 6/1996 | Manna et al. ................. | 604/22 |
| 5,597,899 A | * | 1/1997 | Banner et al. ............... | 530/351 |
| 5,644,585 A | | 7/1997 | Mitchell et al. ............... | 372/25 |
| 6,054,436 A | * | 4/2000 | Crabtree et al. ............... | 514/31 |
| 6,153,383 A | * | 11/2000 | Verdine et al. ................. | 435/6 |

OTHER PUBLICATIONS

Alvarez–Cordero, M.D., Ph.D., "Treatment of Clinically Severe Obesity, a Public Health Problem: Introduction", World J. Surg. vol. 22, 905–906, 1998.

Deitel, M.D., "Overview of Operations for Morbid Obesity", World J. Surg. 22, 913–918, 1998.

Duke, etc., "Cell Suicide in Health and Disease", Scientific American, Dec. 1996.

Korsmeyer, "Regulators of Cell Death", TIG, Mar. 1995, vol. 11, No. 3.

Prins, et al., "Human Adipocyte Apoptosis Occurs in Malignancy", Biochemical and Biophysical Research Communications, vol. 205, No. 1, Nov. 30, 1994, pp. 625–630.

Prins, et al. "Tumor Necrosis Factor–α Induces Apoptosis of Human Adipose Cells", Diabetes, vol. 46, Dec., 1997, pp. 1939–1944.

Prins et al., "Apoptosis of Human Adipocytes In Vitro", Biochemical and Biophysical Research Comm., vol. 201, No. 2, Jun. 15, 1994, pp. 500–507.

Goldman, "Reactions Following Intralesional and Sublesional Injections of Corticosteroids", J.A.M.A., Nov. 10, 1962, pp. 613–616.

Norris et al., "the Influence of Ultraviolet Light on Immunological Cytotoxicity in the Skin", 1997 65(4), pp. 636–646.

1998 TLVs and BEIs Threshold Limit Values for Chemical Substances and Physical Agents Biological Exposure Indices, pp. 155–160.

(List continued on next page.)

*Primary Examiner*—Dinh X. Nguyen
(74) *Attorney, Agent, or Firm*—Sheridan Ross P.C.

(57) ABSTRACT

The destruction of undesired fat cells is achieved by use of a device and method whereby apoptosis inducing factors are delivered to undesired fat cells. Adipose inducing factors, such as UV light, IL-1, TNF and dexamethasone are brought into contact with undesired fat cells through the use of an endoscopic device which facilitates conveyance of such factors to such cells. Repeated delivery of such adipose inducing factors can be achieved by having fiberoptic fibers and/or conveyance tubes left beneath a patient's skin in contact with undesired fat.

5 Claims, 15 Drawing Sheets

OTHER PUBLICATIONS

Faught et al., "Vascular Applications of Lasers", Surgical Clinics of North America, vol. 72, No. 3, Jun., 1992, pp. 681–704.

Norris et al., "Human Keratinocytes Maintain Reversible Anti–Apoptotic Defenses In Vivo and In Vitro", Apoptosis, vol. 2, No. 2, 1997, pp. 136–148.

Kerr et al. "Apoptosis—Its Significance in Cancer and Cancer Therapy", Cancer, vol. 73, No. 8, Apr. 15, 1994, pp. 2013–2026.

Yost et al. "Suction Lipectomy: Outcome Relates to Region–Specific Lipoprotein Lipase Activity and Interval Weight Change", Plastic and Reconstructive Surgery, Nov. 1993, pp. 1101–1108.

Geis et al. Laparoscopic Herniorrhaphy: Results and Technical Aspects in 450 Consecutive Procedures, Surgery, Oct., 1993, pp. 765–774.

Duke, Death of a Cell—Cut '98, pp. 1–14.

Donahoo et al., "Adipocyte Metabolism in Obesity", Metabolism and Nutrition, pp. 501–507.

MacLellan et al., Death by Design Programmed Cell Death in Cardiovascular Biology and Disease, Circulation Research, vol. 81, No. 2, Aug., 1997, pp. 137–144.

Kroemer et al., "Mitochrondrial Control of Apoptosis", Review Immunology Today, vol. 18, No. 1, Jan., 1997.

* cited by examiner

METHOD AND DEVICE FOR DESTROYING FAT CELLS BY INDUCTION OF PROGRAMMED CELL DEATH

RELATED APPLICATION

This application claims priority from U.S. Provisional Patent Application No. 60/082,036, filed Apr. 16, 1998. The entire disclosure of the provisional application is considered to be part of the disclosure of the accompanying application and is hereby incorporated by reference.

FIELD OF THE INVENTION

The present invention is directed toward a method and device for destroying unwanted fat cells by induction of programmed cell death (apoptosis). In particular it relates to a method and device that places substances such as Ultra Violet light (UV) and other chemical substances which induce programmed cell death (suicide cell self destruction) in direct contact with fat cells lying underneath the skin.

BACKGROUND OF THE INVENTION

The desire of individuals to lose weight and specifically, to lose fatty tissue, has become nearly an obsession in the United States and many other countries. Any simple and safe method toward achieving a slim figure is in great demand. Methods for losing weight include hundreds of advised diets, machines and methods for exercise, various psychiatric techniques involving alteration in mental attitudes, and a variety of surgical techniques. Liposuction has created an entirely new surgical cosmetic industry, but carries a small but significant risk and often leaves the patient with an unsightly cosmetic result due to the inflammatory reaction surrounding where the fatty tissue has been removed by a technique which produces a severe tissue reaction.

Obesity is a serious public health hazard, second in importance only to tobacco. Approximately ⅓ of Americans are seriously overweight according to life insurance data. In approximately 12 million Americans, obesity significantly contributes toward the cause and complications of serious disease. Such conditions include heart and lung disease, many types of cancer, diabetes, high blood pressure, and peripheral arterial disease. This is in addition to how obesity becomes a cosmetic problem. Being overly fat limits both length of life and its quality.

A multi-billion dollar industry has developed in an effort to control weight. The many varied and expensive techniques employed speak to the relative ineffectiveness of the many techniques that have been tried to get rid of excess fat.

Obesity has recently been recognized as a public health hazard of epidemic proportions by the World Health Organization. One of three Americans between the ages of 20–74 are obese (Body Mass Index >30 Kg/m$^2$ body surface). This amounts to 58 million people. The number of obese adults has increased dramatically. In 1980 25% of US adults were obese. The equivalent figure was 33% in 1990. In Europe the equivalent figure is about 40%.

Obesity significantly contributes to the dangers of other diseases in approximately half of those who exceed the threshold description of obesity. For example, 19% of the cost of management of heart disease can be ascribed to obesity. Obesity is also recognized as a co-morbid factor for obese patients suffering from degenerative arthritis, peripheral vascular disease, and many forms of pulmonary disease such as emphysema. The expenditure for products, goods, and services in the management of obesity is estimated to be $33 billion per year. This is 3%–4% of total health care expenditure per year and exceeds that expended for AIDS and cancer.

Obesity is such a prevalent, important and distressing problem that its many methods for suggested management are too well known to deserve more than listing. They include diets that exclude fats and high caloric elements, food supplements, appetite suppressants, exercise machines and regimes, biofeedback and other psychotherapeutic techniques, and a variety of operative techniques. Operations include a number of methods for decreasing the capacity the stomach, gastric by-pass operations, methods to shorten the small intestinal absorption surface, excision of the unwanted fat (lipectomy) and techniques of liposuction. Liposuction is performed approximately 51,000 times each year in the US. The maximum amount of fat that can safely be removed is approximately 2 Kg. Being an operative technique for removing fat, in this case by suction, it inevitably excites an inflammatory response at the operative site, which results not only in post operative inflammation but in subsequent uneven and unsightly scarring beneath the skin where the fat has been removed. Numerous patents involve devices and techniques of liposuction. For example, U.S. Pat. No. 5,527,273 to Manna et al. discloses an ultrasonic lipectomy probed; U.S. Pat. Nos. 5,642,270 and 5,644,585 to Mitchell et al. disclose the use of a yag laser to ablate tissue; and U.S. Pat. No. 5,143,063 to Fellner discloses the use of heat to non-invasively destroy adipose tissue. Such methods which destroy cells by heat, laser or ultrasound or by liposuction of direct trauma, are relatively crude in that they involve rough manipulation of body tissue fat cells and therefore incite severe local inflammatory reaction. This results in scarring and other immediate and longer term pathologic reactions. Such adverse reactions add to the probability of immediate complications (morbidity and sometimes even mortality) and to a poor subsequent cosmetic result at the site of the inflammatory response.

In every person hundreds of thousands of old or damaged cells die each day by the process of apoptosis and are replaced in the ebb and flow of maintaining a constant number of living cells in the body. Old and damaged cells die in response to a signal triggered on the cell surface for the targeted cell to self destruct (commit suicide). A popular synonym for this process is programmed cell death. Such cell turnover occurs without causing tissue reaction. Apoptosis is the body's mechanism for cell disposal which maintains a balance between the removal of old cells and their replacement by new cells. Some cell types are quickly replaced. Others, including brain, nerve and to a lesser degree fat cells, lack in varying degrees the potential for self renewal. Fat cells promptly increase or decrease in individual cell size in response to overeating or diet, but have at best limited self renewal potential.

The signal triggering cell surface receptors that induce cell suicide are highly specific for each cell type. Within the past two decades there has been intense study of factors which stimulate apoptosis, particularly as they provide a potential for destruction of cancer cells. Each cell type has its own specific receptor which can be activated or blocked.

Cell self destruction by apoptosis must be differentiated from destruction by outside forces such as direct injury, infection, or heat-each of which produces cell destruction which results in cell necrosis and scarring. Apoptosis can be differentiated from necrosis by microscopic and specific chemical analytic methods. Necrosis results in the familiar signs of inflammation including swelling, redness, pain and tenderness. Apoptosis does not stimulate such reactions. The cells shrivel up, break into pieces and the contents are quietly removed by methods that do not induce inflammation.

Therefore, a need exists for a method and a device to eliminate undesirable adipose tissue in a safe, inexpensive and efficient manner without inciting violent local tissue reaction such as occurs following liposuction removal of fat cells, or by their destruction by heat, laser, ultrasound or other similar methods. There is also a need for a method and device that can destroy undesired fat cells by stimulating apoptotic events in fat cells, thus ridding a patient of undesired fat without the harmful reactions experienced by present fat-removal techniques and procedures.

SUMMARY OF THE INVENTION

The device and technique of the present invention does not incite the above described deleterious reactions. Instead, apoptosis is triggered by activation of a signal mechanism on the surface of a cell which commands the cell to self destruct. An important mechanism in apoptosis involves cutting off the energy supply to cell function. The present invention is a new method for ridding the body of excess unwanted body fat using a temporarily implanted device placed adjacent to the targeted fatty areas. The device delivers chemical or light signals to the fat cells to self destruct by a recognized physiologic pathway termed apoptosis. This is the mechanism by which the body ordinarily disposes of old or damaged cells, without inciting an inflammatory reaction.

The present invention provides a means by which depots of unwanted excess fat in the body can be stimulated to destroy themselves by. The present invention applies signals directly onto the surface of targeted unwanted fat cells to undergo such self destruction or apoptosis.

Apoptosis is like cutting off the gasoline supply to the cylinders of an automobile. It simply stops functioning. Cell damage by heat, laser, ultrasound or direct surgical trauma is like the damage from outside forces to the entire automobile. Cells made to commit suicide by apoptosis merely shrivel up and automatically decompose, inciting no inflammatory reaction and leaving no more trace than does atrophy of other aged or slowly dying tissue.

The device and method of the present invention induces programmed cell self-destruction (apoptosis) in unwanted fat cells by activating mechanisms on the surface of the cell which start a chain of reactions which prompt the cell to self destruct. Apoptosis is a relatively recently discovered mechanism by which cells of various types are induced to "commit suicide" by specific mechanisms. The process is the one the body uses to remove aged or dying cells thousands of times every day as younger cells take their place. Apoptosis can be induced or inhibited by several signaling mechanisms. In general, a receptor on the surface of the cell serves as a switch which starts a series of subsequent signals within the confines of the cell which shortly thereafter stops the biochemical machinery which supports cell function, causing such cells to die. Apoptosis has been called the command which orders the cell to die by suicide. It apparently does so by blocking the energy mechanisms within the mitochondria situated within the cell. Cut off from its energy by apoptosis, the cell shrivels up and disintegrates in a fashion that can be identified on microscopic examination. Such apoptotic degeneration differs markedly from the appearance of cells killed by heat or other direct injury. Neither does it require the participation of immune responses from other defending cells within the body.

Each type of cell has a particular resistance or sensitivity to its own apoptotic signaling mechanism. Some cells, such as certain types of thymocytes (circulating white blood cells) are sensitive to UV radiation. Many other cells are more resistant. Like a specifically designed key, the apoptotic triggering mechanisms are usually uniquely designed for each cell type. The substances used for signaling fat self destruction are those found to be effective for fat cells.

The present invention introduces AIF (apoptosis inducing factors) directly onto the pad of fat that lies beneath the skin. The command for fat cell destruction is thus focused specifically on the fat cells intended for destruction. This is achieved by inserting an endoscope, such as is now commonly used for performing removal of diseased gall bladders or in so called minimal access repairs of inguinal hernia or in some patients requiring appendectomy. Such commercially manufactured endoscopes are used hundreds of thousands of times a year in various types of operations. They consist of small diameter plastic tubes, fitted with a light source and a tiny television camera at the tip which permit performance of operative procedures at the end of the scope under direct visions through another small caliber tube. Because their use requires only two or more very short (1–2 centimeter) skin incisions for their insertion, their use is referred to as minimal access surgery. The device of the present invention can be viewed as modified existing laparascopes so they deliver apoptosis inducing factors directly onto the fat cells located beneath the intact skin.

The present device is introduced through a small 1–2 cm skin incision. Once positioned beneath the skin, a plane is developed between the overlying layer of fat and the separated layer of fascia and underlying muscle. Using a technique now frequently used in minimal access inguinal hernia repair, the space is enlarged by use of a distending balloon which raises the skin and fat off the firm floor consisting of fascia and muscle. Only an infrequent small blood vessel transverses this space developed by the balloon. When bleeding occurs it can be stopped either by pressure or with an operating cautery. Most of the blood supply to the subcutaneous fat comes from the overlying skin, not from below. A wide subcutaneous space is thus created by the endoscope for deploying the AIF delivery system onto the overlying layers of fat. Although the technique above described develops a plane beneath the anterior abdominal wall, the same device can be used to approach fat located in other areas of the body, such as in the retroperitoneal space where fatty tumors often develop. The present invention delivers a signal for the targeted fat cell to self destruct without the harmful reaction of removal by ordinary operative or other types of injury. In one embodiment, because the device is temporarily left adjacent to the underside of the targeted fat, the apoptotic signal which triggers fat destruction can be repeated for as long as fat destruction is indicated. At the end of treatment the device is removed. The specific signals delivered are those proven to stimulate fat cells to self destruct and as delivered to this confined site are of proven safety to other tissues. Both chemical and special wave length light can be used, separately or in combination, as apoptotic signals.

In another embodiment of the present invention, a targeted stimulus to fat cell self destruction is achieved by transmitting the chemical or light source apoptosis stimulus from outside the body to the site of the unwanted fat through a short skin incision using plastic tubes for the admission of soluble chemical stimulants and fiberoptics for the transmission of light signals. The biologically unreactive tubes or fibers lead from outside the body through a tunnel beneath the skin and fat to the undersurface of the targeted fat. The signals which by-pass the skin, deliver the signals directly on to the unwanted fat. Because the device is made of and/or covered by biologically unreactive materials, it can be left in place for a prolonged period. This permits continued or pulsed delivery of the apoptosis signals to the targeted fat for as long as necessary to destroy the fat depot. When the desired amount of fat has been destroyed, the device can be removed by simple endoscopic surgical techniques.

Two general categories of apoptosis inducing factors (AIF) are used in the currently described technique: The first is Ultra Violet light (UV); the second consists of chemical substances proven to induce apoptosis of fat cells. UV is a well known component of sunlight. Under ordinary conditions the skin blocks UV light from substantially penetrating to the underlying fat. The present device by-passes the protective layer of skin overlying the pad of unwanted fat, and transmits the UV beam directly onto the targeted fat through an endoscope inserted a short distance from the target fat. The UV light is transmitted through the scope via fibers capable of transporting such light. The device thus flanks the protecting skin which ordinarily blocks the apoptotic inducing UV from contact with the mass of underlying fat cells. The suicide signal is thus delivered to the unwanted fat cells via the back door to the fat cells, despite the protective coat of the overlying skin.

Ultra violet light induces apoptosis in certain types of lymphocytes and in keratinocytes in the skin. The latter provide most of the protective function of the skin to underlying tissues. Red light (wave length 1 m to 760 nm) and Ultra violet light (wave length 760 nm to 180 nm) are known as non-ionizing radiation in contrast to X-rays which have a shorter wave length and have far more toxic potential. Both Ultra Violet (UV) and Infra Red (IR) light are used extensively in industry and in clinical practice. Safe levels of exposure to both UV and IR are defined by the American Conference of Governmental Industrial Hygenisists (ACGIH). Such limits are expressed in Threshold Limit Values (TLV) and Biological Exposure Index (BEI).

Both UV and Red and Infra red lasers are used extensively in clinical practice. Lasers are used to destroy targeted tissue by high energy highly focused beams of light of a single and congruent wave length focused on tissues that are targeted for destruction. Their most common use is to destroy tumor tissue or to burn highly focused holes in the atherosclerotic plaques that plug up small blood vessels (endarterectomy). Such high energy beams are in direct contrast to the low energy exposure in the embodiment in which necrosis is avoided and the targeted cell is induced to undergo self destruction by apoptosis. Knowledge of laser generation and transmission can be utilized for delivering much less intense beams into the body in the embodiment.

IR can be generated from Light Emitting Diodes using minute amounts of electricity. This is the familiar source of red or white lights on the dashboard of an automobile, or the ON-OFF signal on a toaster or microwave oven, wrist watch or computer. IR is transmitted by many types of fiberoptics. Skin effectively blocks transmission of most of the sun light to the fat and other underlying tissues.

By the use of fiberoptics, one embodiment of the present invention takes UV or other light from an extracorporeal source and transmits it directly to the under surface of fat beneath the skin. The fibers run from the emitting source outside the body through a small incision in the skin remote from the targeted fat area, through a subcutaneous tunnel to the undersurface of the targeted fat.

In one embodiment as pictured in FIG. 4, an endoscope is inserted into the space in the right lower quadrant to provide visualization of the space as the device is being positioned as it emerges from the tube in the right upper quadrant. The port on the patient's left provides access of a forceps manipulated by an assistant in positioning of the device. In another embodiment (FIG. 8), the delivery tubes lie on top of the pad; a suction catheter for removal of freed fat and dead cell debris lies at the base and beneath the pad on which the tubes are anchored.

The UV or IR light apoptosis stimulants are generated outside the body, transmitted by special fiberoptics, led into the body through a small skin incision into an endoscopically created tunnel to the surface of the targeted fat, where the light beams are concentrated on the targeted fat. An underlying impenetrable biologically unreactive plastic skirt protects the underlying fascia and muscle from the light exposure.

In other embodiments of the present device and technique, agents in solution or suspension that are known to induce fat cell apoptosis are delivered directly onto the surface of unwanted fat cells via the uniquely designed endoscope of the present invention. Some such substances activate (or block) triggering mechanisms on the surface of the targeted cell. Others alter the molecular configuration or orientation of the surface cell receptors. Still others seem to work by stimulating or blocking the messengers that run from the cell surface to the packages of energy (mitochondria) within the wall substance. The end result often is disintegration of the DNA within the nucleus of the cell, which shortly thereafter causes cell disintegration.

The chemical apoptosis stimulants used in the present invention are those proven effective in provoking fat cells self destruction. The fluid conveying the stimulant to the fat cell serves to irrigate and by a suction catheter to remove the damaged and dying fat cells. A wide underlying protective plastic skirt and a suction catheter protects the underlying fascia and muscle from significant influence of the apoptotic stimulant.

An extraordinary variety of molecules are of proven effectiveness in triggering apoptosis in specific cell types. Each cell type has its unique stimulating molecule which like a key in a lock fits its cell surface receptor which sends a self destructive signal to the nucleus or the mitochondria to self destruct, including but not limited to those set forth in 4) Korsmeyer, *SJ in Trends in Genetics*, Vol II, No 3, 101–105, March 1995. The mitochondria is the power source for cell metabolism. When the energy source is interrupted, metabolism stops and the cell disintegrates.

Certain uniquely designed embodiments of the present device permit extension of the delivery time of the AIF. At its simplest, the AIF, whether UV or a chemical substance, can be delivered all at one time while the scope is in place immediately below and in contact with the fat cells. This requires precise control of the dose schedule so it will remove only the precise amount of fat desired. Alternative embodiments involve leaving the delivery system in place beneath the overlying pad of fat, so that if the first administration of the AIF has not resulted in sufficient fat cell apoptosis, additional administrations of AIF can be delivered. One of skill in the art will appreciate the dosages and administration regimens required to affect layers of fat in a fashion to remove such fat from a patient's body. by induction of fat cell apoptosis, and in particular is directed to a method and device that delivers a chemical or light signal to fat cells to cause such cells to self-destruct.

The effects of both chemical apoptosis stimulants and light stimulants can be enhanced by special procedures, such as changing the chemical environment of the target fat, or when light stimulants are used, for example, by staining the fat with dyes which enhance the effects of the transmitted light.

DETAILED DESCRIPTION OF PREFERRED EMBODIMENTS

Figure 1:
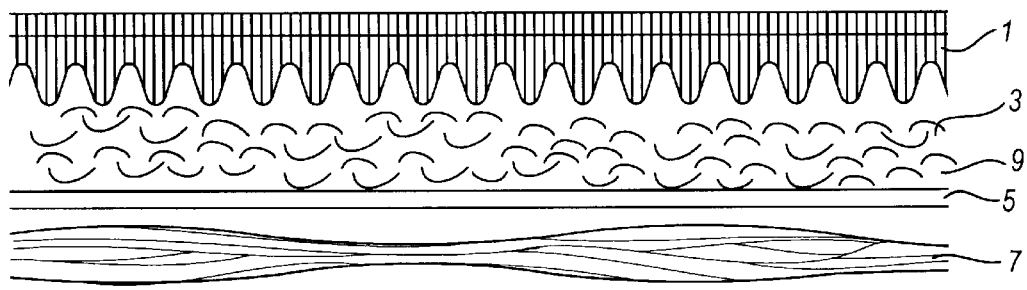
FIG. 1 shows the anatomy of the skin and underlying fat, fascia and muscle and where the present device is placed and how it lies in contact with the subcutaneous fat and above the underlying fascia and muscle.

The present invention is used to rid the body of unwanted depots of fat by a hitherto unused method of stimulating the fat cells to commit suicide or self destruct. Signals are delivered to the surface of unwanted excess fat cells to cause self destruction or suicide of such cells. This relatively recently discovered process, known as apoptosis, is the mechanism by which the body destroys old or damaged cells within the body many thousands of times each day. It has the unique property of not causing tissue irritation or reaction, in contrast to other existing methods of destroying fat cells. Apoptosis differs entirely from the better known mechanism of cell destruction following cell injury from burns, direct trauma, following infection from bacteria or viruses, or immune responses, all of which produce destruction of surrounding tissue and consequent scarring and disfigurement. The pathological reaction of apoptosis differs markedly from necrosis, which term applies to the reaction of tissue following mechanical cell destruction. Apoptosis has not previously been suggested for removal of fat.

In every person hundreds of thousands of old or damaged cells die each day by the process of apoptosis and are replaced in the egg and flow of maintaining a constant number of living cells in the body. Old and damaged cells die in response to a signal triggered on the cell surface for the targeted cell to self destruct (commit suicide). A popular synonym for this process if programmed cell death. Such cell turnover occurs without causing tissue reaction. Apoptosis is the body's mechanism for cell disposal which maintains balance between removal of old cells and their replacement by the new. Some cell types are quickly replaced. Others including brain, nerve and to a lesser degree fat cells, lack in varying degrees the potential for self renewal. Fat cells promptly increase or decrease in individual cell size in response to overeating or diet, but have at best limited self renewal potential.

The signal triggering cell surface receptors to induce cell suicide are highly specific for each cell type. Within the past two decades there has been intense study of factors which stimulate apoptosis, particularly as they provide a potential for destruction of cancer cells. Each cell type has its own specific receptor which can be activated or blocked.

Cell self destruction by apoptosis must be differentiated from destruction by outside forces such as direct injury, infection, or heat—each of which produces cell destruction which result in cell necrosis and scarring. Apoptosis can be differentiated from necrosis by microscopic and specific chemical analytic methods. Necrosis results in the familiar signs of inflammation including swelling, redness, pain and tenderness. Apoptosis does not stimulate such reaction. The cells shrivel up, break into pieces and the contents quietly removed by methods that do not induce inflammation.

Two types of signals are used in the present method to stimulate fat cells to self destruct: one chemical and the other ultra violet light. Each has the property of specifically stimulating the fat cell surface receptor to initiate programmed cell self destruction. Using these two types of apoptosis triggering mechanisms, the present invention uses minimal access surgical and fiberoptic techniques to deliver or transmit the self destruct messages directly on to the surface of the targeted fat cell.

In the present invention, safe exposure levels of UV are utilized, such levels well defined by the American Conference of Government Industrial Hygienticists, 1998 edition. Ultraviolet light induces apoptosis in certain types of lymphocytes and in keratinocytes in the skin. The latter provide most of the protective function of the skin to underlying tissues. Redlight (e.g., wavelength 1 m to 760 nm) and ultraviolet light (wavelength 760 nm to 180 nm) are known as non-ionizing radiation, in contrast to x-rays, which have a shorter wavelength and have far more toxic potential. Both ultraviolet and infrared light are used extensively in industry and in clinical practice. Safe levels of exposure to both UV and IR are defined in well recognized references. Such limits are expressed in threshold limit values (TLV) and biological exposure indexes (BEI). In contrast to prior art systems which use high energy, highly focused beams of light of a single and congruent wavelength to target tissues for destruction, the present invention uses low energy exposure so that necrosis is avoided and the targeted cell is induced to undergo self-destruction by apoptosis. IR can be generated from light emitting diodes using minute amounts of electricity and can be transmitted through known light sources, including fiber optics. Fiber optics are used in the present embodiment to deliver UV or other forms of light from an extracorporeal source and transmits it directly to the undersurface of fat beneath the skin. The fibers run from the emitting source outside the body through a small incision in the skin remote from the targeted fat area, through a subcutaneous tunnel to the under surface of the targeted fat.

When using UVB wavelength, approximately 308 nm is used, with the threshold limit value (TLV) being 120 m Joules/cm$^2$. The relative spectral effectiveness (RSE) of S Lambda is 0.026 Fluence Value, which varies with time of exposure.

Because fat often accumulates in unwanted volume beneath the skin over the anterior abdomen, this site is used as illustrative in describing the technique of the present invention. The same techniques, however, are applicable for excess fat elsewhere in the body, such as beneath the skin of the thighs, buttock, breast, neck, in the area behind the peritoneum (retroperitoneal fat), or even within the peritoneal cavity (omentum). We have shown that apoptosis can be induced in mouse adipocytes in tissue culture by various stimuli including dexamethasone, tumor necrosis factor, and ultra violet light having a wave length of about 308 nm.

The endoscope of the present invention is based upon the design of similar scopes widely used for a number of operations. A standard endoscope and methods for using such endoscope can be utilized with the present invention, such endoscope typically having a catheter through which is provided an introducer, such as a needle, fiber optic fibers, etc. It is, however, uniquely altered to deliver apoptosis inducing substances or factors (referred to herein as AIS or AIF) to fat tissue rather than solely for performance of surgical operations. The present device has a diameter similar to commercially available operating scopes. Its eye piece and TV transmitting system is substantially the same as commercially available instruments. The methods for introducing and using the device for manipulating the tissue beneath the skin will be straight forward to one of skill in the art.

The preferred scope device of the present invention closely resembles the surgical endoscope used for minimal access inguinal hernia repair. Preferably, the distensible balloons for creating a space beneath the skin and fat is of greater length and breadth so that a wide expanse of fat tissue is exposed, in contrast to the smaller balloon used in visualizing the area needed for inguinal hernia repair. For use in removing fat from the anterior abdominal wall, the device is preferably inserted through small (1–2 cm) skin incisions.

Sources for delivery of UV light (preferably the beta component) include extracorporeal commercially available sources where both the intensity and duration of the UV can be carefully controlled. In contrast to removal of fat cells by heat, the present device uses UV in a fashion that is not intended to raise the temperature of the fat cells more than a few degrees centigrade. The tip of the scope can be fitted with a temperature sensor to cut off power when temperature exceeds a given maximum.

Although the description of the device above is principally designed for removal of abdominal fat, the device can be used anywhere in the body where unwanted fat cells are present. This includes use on benign fat cell tumors (lipomas), or for malignant tumors called liposarcomas, which frequently are situated either in the extremities or in the retroperitoneal space. Special tips for carrying UV or other AIF can be devised for each anatomic demand.

Induction of apoptosis must be differentiated from mechanical methods for cell destruction such as the heat destruction by cautery, laser destruction, ultrasonic destruction or suction removal of fat cells, all of which create a wide and intensive tissue reaction. The typical signs of inflammation (heat, pain, mass and redness) do not occur following induction of apoptosis. Following induction of apoptosis, the cell membrane contracts, the intracellular sources of energy (from mitochondria) stop functioning, the nucleus DNA begins to disintegrate and when the cell breaks down, the ordinary body mechanisms for disposing of hundreds of thousands of cells that die each day sweep away the debris without reaction.

The endoscope used with the present invention (and its attachments) are adaptations of the scopes used in inguinal hernia repair, except made longer (e.g., 25 cm) to deploy the AIFs over the maximum area of fat to be removed. The space beneath the blanket of fat can be created either by blunt dissection using the end of the scope cauterizing the occasional blood vessel that enters the fat from below, or by insufflation of carbon dioxide as a dissecting agent, or by a specially designed balloon that will fit beneath the entire area of fat to be subjected to AIFs including UV light. The balloon is preferably made of a non-biologically active plastic such as Goretex®, since it is intended to be left in situ for several days or weeks for possible use when additional administration of UV or other AIF is required. The balloon is constructed preferably with fibers on its superior surface for delivery of UV, and when used to deliver soluble apoptotic substances, it includes with porous semipermeable tubes.

Chemical substances can be delivered through the device to fat cells targeted for self destruction via semipermeable porous small diameter delivery tubes, which slowly leak their contents into the surrounding tissues. Such solutions are delivered via a low volume pump into the tubes running through the endoscope to the area beneath the fat. The impermeable tube leads to a wide pore size permeable tube at the site of AIF delivery. PTFE (e.g. Goretex®) can be configured in this fashion. Such delivery tubes can be deployed along the surface of the fat cells as described above for fiber optic transmission of UV.

A combination of UV and chemical AIF can be used by altering placement of fiber optics with hollow tubes containing solutions of AIF as described.

Substances used to induce fat cell apoptosis, and their sites of action, have been well summarized in the literature. Examples include those disclosed by Duke, R. C. et al., "Cell Suicide and Health Disease," Scientific American, December 1996, pp. 50–87; Stanley, J., "Regulators of Cell Death," Trends in Genetics, Vol. II, No. 3, March 1995, pp. 101–105; and Kroener, G., et al., "Mitochondrial Control of Apoptosis," Immunology Today, 18, No. 1, January 1997, pp. 44–52, all of such references incorporated herein in their entireties by this reference. In one embodiment, a combination of such apoptosis inducing substances include UV, dexamethasone, IL-2 and TNF.

The present invention is thus directed to a method and device for destroying adipose tissue by induction of programed cell death (e.g., apoptosis) by triggering the mechanisms on the surface of and within adipose tissue cells that cause such apoptotic events. The present invention stimulates fat cell to self destruct without the application of destructive heat energy or the physical removal of fat cells from a person's body. Although in some embodiments of the present invention UV energy can be focused onto particular areas of adipose tissue to trigger desired apoptotic events without any incision being made, in a particularly preferred embodiment, subcutaneous direct contact between adipose-inducing factors, such as UV light with undesired adipose tissue is relied upon to initiate apoptotic reactions in antipose cable. The transmission of UV light onto undesired adipose tissue can be achieved by insertion of an endoscope device through a person's skin either above or below, but preferably below, adipose tissue to be irradiated with UV light. UV light is then conveyed through the endoscope, preferably by the use of fiber optic fibers, so that UV light of appropriate frequency and intensity is transmitted onto undesired adipose tissues. Care is required to avoid undesired contact with other types of tissues (e.g., skin tissue, muscle fibers, etc.).

Any appropriate energy source can supply the UV energy. Moreover, localizing or focusing elements can be used, preferably sources and elements that do not contribute significantly to heat or radiant energy that may cause undesired damage to tissue. The particular amount of UV energy and duration of contact with adipose tissue will vary with particular physiologies of individual subjects, including such factors as body weight, health, age, sex, thickness of adipose tissue, type of adipose tissue, as well as other factors.

Different tip configurations of an appropriate endoscope can be fashioned for different areas of the body. For example, in cases where removal of facial deposits are required, more narrow, bullet-shaped tips can be utilized so that the end of the endoscopic probe may be placed closer to delicate nerve bundles without the risk of damage to tissue other than adipose tissue. As can be seen in the various figures, particular designs of endoscopic tip ends can be utilized to achieve desired direction of UV light onto adipose tissue and away from other types of tissue. Thus, in one particular embodiment, fiber optic fibers can have cladding removed from particular surfaces of the fiber optic fibers so that ultraviolet light can be transmitted along the extent of the fiber and/or at appropriate periodic points long such fiber. Cladding would remain in place, however, to protect underlying muscle tissue.

In still other embodiments, filters can be utilized to regulate the frequency of light to be transmitted and to absorb other wavelengths of light that are undesired. Thus, various lenses having particular cut offs at undesired wavelengths can be employed with the endoscopic device during the transmission of UV light through the fiber optic fibers. As can be appreciated, the selection of a particular filter will be based on the desired operating parameters and will be selected so that thermal lensing effects are minimized. The intensity of UV radiation should not be such that it would cause outright ablation of tissues, such as is used in laser systems for precise continuous incisions, vaporization and/or emulsification of biological material.

Although fiber optic fibers are preferably utilized, other light transmitting vehicles can be used, such as hollow waveguides. Such waveguides often include multi-layer dielectric coatings to enhance transmission. It will be appreciated that the UV light used in the present method has high absorption and short penetration depths and thus, the UV radiation can be accurately targeted at undesired adipose tissue without generating undesired heating of the tissue.

Sensors can be utilized to provide feedback for maintaining a selected power level and for measuring temperatures during an apoptotic procedure. Indeed, analog or digital controllers, such as a computer with software, can be utilized to appropriately adjust power outputs, concentrations of AIFs, etc., in appropriate amounts in order to maintain desired transmission of apoptotic inducing factors, such as UV light. The ultraviolet light utilized is preferably in the B-wave band, quantitated by time and intensity by standard UV measurement.

In one embodiment, a plastic sheet containing UV fibers or capillary drip irrigation tubes are left in situ awaiting the possible need of a subsequent stimulation of apoptosis. The ends of the fibers or capillary tubes are preferably wrapped in a small, tight-fitting, non-reactive plastic (PTFE) and left beneath the skin at a distance from the area of fat removal. Non-reactive plastic sheets are preferably made of Goretex® as are used for long term implantation in many types of hernia repair. Plastic tubes used for drip irrigation are preferably PTFE Goretex® manufactured with pore sizes that allow AIF fluid to leak at a slow but constant rate under a constant extracorporeal pump pressure onto the fat adjacent to the tubes. Balloons will be shaped appropriately for particular fatty areas of a person's body and can be deployed through the scope in a manner similar to that used in hernia repair.

In various embodiments of the present device, the device is made of and/or covered by biologically unreactive materials which can be left in place inside the body for prolonged periods of time. This permits continued or pulse delivery of apoptotic signals to the targeted fat for as long as necessary to destroy the fat deposit. When the desired amount of fat has been destroyed, the device can be removed by simple endoscopic surgical techniques. Devices of the present invention include those specifically using apoptosis-inducing chemicals in solution and others are directed to the transmission of light stimulants to promote apoptosis. Still other devices combine these two techniques. In delivering chemical apoptotic agents, a fluid is conveyed carrying the stimulant to fat cells and serves to irrigate such cells. A suction catheter removes the damaged and dying fat cells undergoing apoptosis. A wide underlying protective plastic skirt and a suction catheter are utilized to protect the underlying fascia and muscle from significant influence of the apoptotic stimulant.

In other embodiments, the UV or IR light apoptosis stimulants are generated outside the body, transmitted by special fiber optics, lead into the body through a small skin incision into an endoscopically created tunnel to the surface of the targeted fat, where the light beams are concentrated on the targeted fat. An underlying impenetrable biologically unreactive plastic skirt is preferably used to protect the underlying fascia and muscle from the light exposure. The effects of both chemical apoptosis stimulants and light stimulants can be enhanced by special procedures, such as changing a chemical environment of the targeted fat, or when light stimulants are used, by staining the fat with dyes which enhance the effects of the transmitted light.

Substances other than UV light that can be used to induce fat cell apoptosis include those substances that induce apoptosis (or that limit apoptosis) and can be found in the literature, for example, Duke, R C et al., "Cell Suicide and Health and Diseases", Scientific American, December, 1996, pp. 80–87; Stanley, J., "Regulators of Cell Death", Trends in Genetics, Vol. II, No. 3, pp. 101–105, March, 1995; and Kroemer, G., et al., "Mitochondrial Control of Apoptosis", Immunology Today, 18, No. 1, pp. 44–52, January, 1997, all of such references incorporated herein in their entireties by this reference.

In one embodiment, a combination of AIFs can be used, for example, carefully administered doses of UV, dexamethasone, IL-1 and TNF can be used to induce fat cell apoptosis. The amounts and doses of any particular agent and/or application will vary with the particular person, adipose tissue, etc., but such parameters will be known to those of skill in the art based upon the teachings herein in combination with standard procedures employed in the use of such substances.

FIG. 1 illustrates the anatomy of the anterior abdominal wall. The skin (1) acts as a protective shield to the underlying tissues which include the subcutaneous fat (3) and the fascia (5) and muscle (7) which lie below the skin. The fat lies as a pad over the fascia with a potential relative avascular (bloodless) space (9) between the two tissues. This potential space resembles the potential space between a blanket (the fat) and an underlying cotton sheet on a bedspread.

Figure 2:
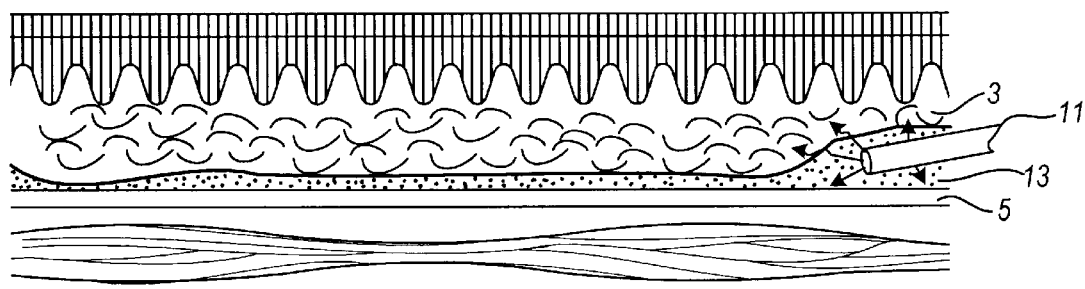
FIG. 2 illustrates the endoscopic surgical development of the space between the fat and the underlying fascia and muscle where the device is placed, created using either the endoscope or insufflation of carbon dioxide.
Figure 3:
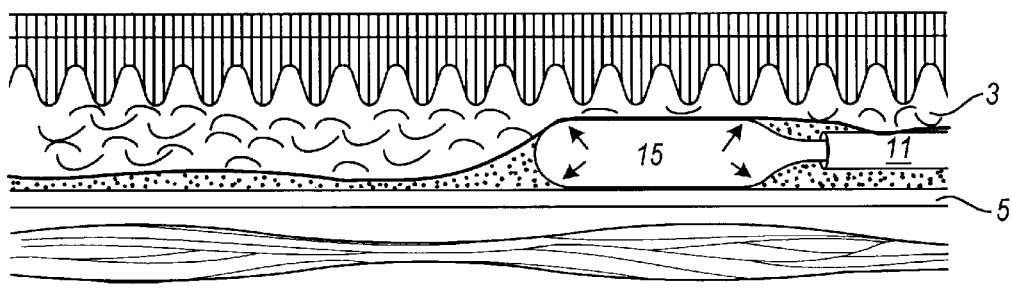
FIG. 3 illustrates how an inflated balloon can be used to develop a space beneath the fat where the device is to be positioned.

FIG. 2 illustrates how this potential space between the fat and the underlying fascia can be developed into an actual space using blunt dissection or an endoscope (11). Such a space beneath the fat of the anterior abdominal wall is developed by surgeons in performing certain types of groin hernia operations. The space has only a few small blood vessels crossing it, and these vessels are easily sealed through the endoscope when the space is being developed. This creates a bloodless space (13), like a tent, with a fat pad as its roof and the fascia as the floor. Surgeons sometimes use an inflatable balloon (15) at the end of the endoscope (FIG. 3) or carbon dioxide gas under slight pressure to develop this space. The various forms of the devices that can be used with the present method are positioned in this space. Their superior surfaces thus lie in direct contact with the targeted layer of fat.

Figure 4:
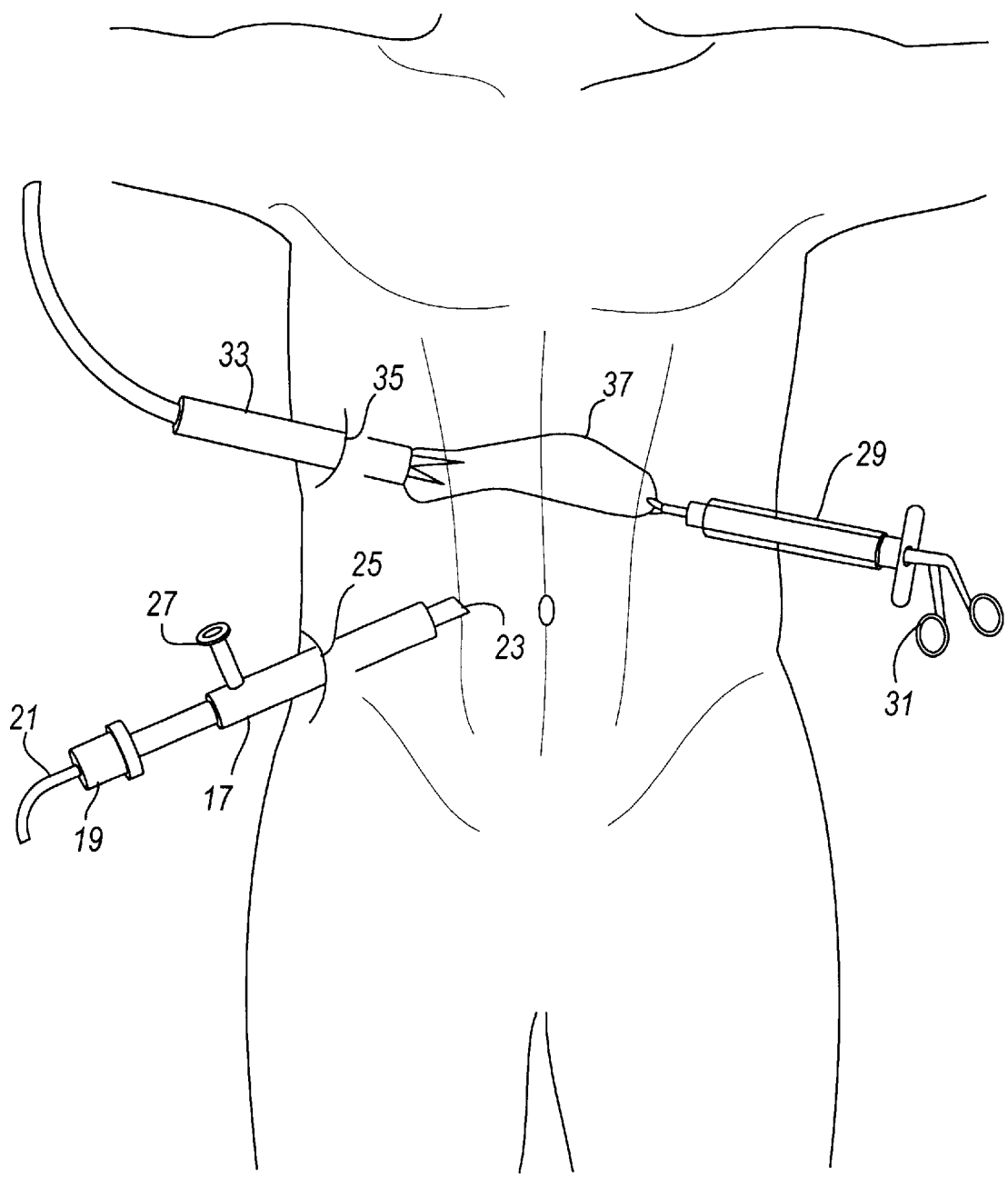
FIG. 4 illustrates how the device is inserted through a tube in the patient's right upper quadrant of the abdomen into the space beneath the skin and fat.

Since the fat rests largely as an unattached layering on the fascia around the circumference of the body, a tube can be run through a small diameter hole from the device within the developed space to a location remote from the targeted fat area where the tube emerges from the body through a small incision FIG. 4 illustrates how the device is inserted into the space beneath the fat. These are well established endoscopic surgical techniques used in many types of operations. A tube (17) in the right lower quadrant carries the electronic components to the miniaturized TV camera (21) and light source (23) at the end of the tube. The components pass into the space beneath the skin through a small skin incision (25) in the anesthetized patient's right lower abdominal quadrant. A side arm in this endoscope (27) can be fitted to a carbon dioxide gas source to keep the fatty roof of the "tent" overlying the fascia from collapsing while the device is being placed. In fact, this is seldom necessary.

A small diameter (5 mm) tube (29) is placed in the patients left upper abdominal quadrant for use by the surgeon's assistant in holding tissue in counter traction, or in pulling the device into position with a special forceps (31) small enough to fit into the lumen of this endoscopic tube. This is also according to standard minimal access or endoscopic surgical techniques.

A third endoscopic tube (33) enters the subcutaneous space through a small skin incision (35) in the patient's right upper quadrant. The rolled up compressed device (37) is inserted through the lumen of this 2 cm diameter tube.

In FIG. 4 the device is shown exiting the lumen of the tube within the subcutaneous space beneath the fat. The forcep (31) manipulated by the surgical assistant in the left upper quadrant, is pulling the device into position.

Figure 5:
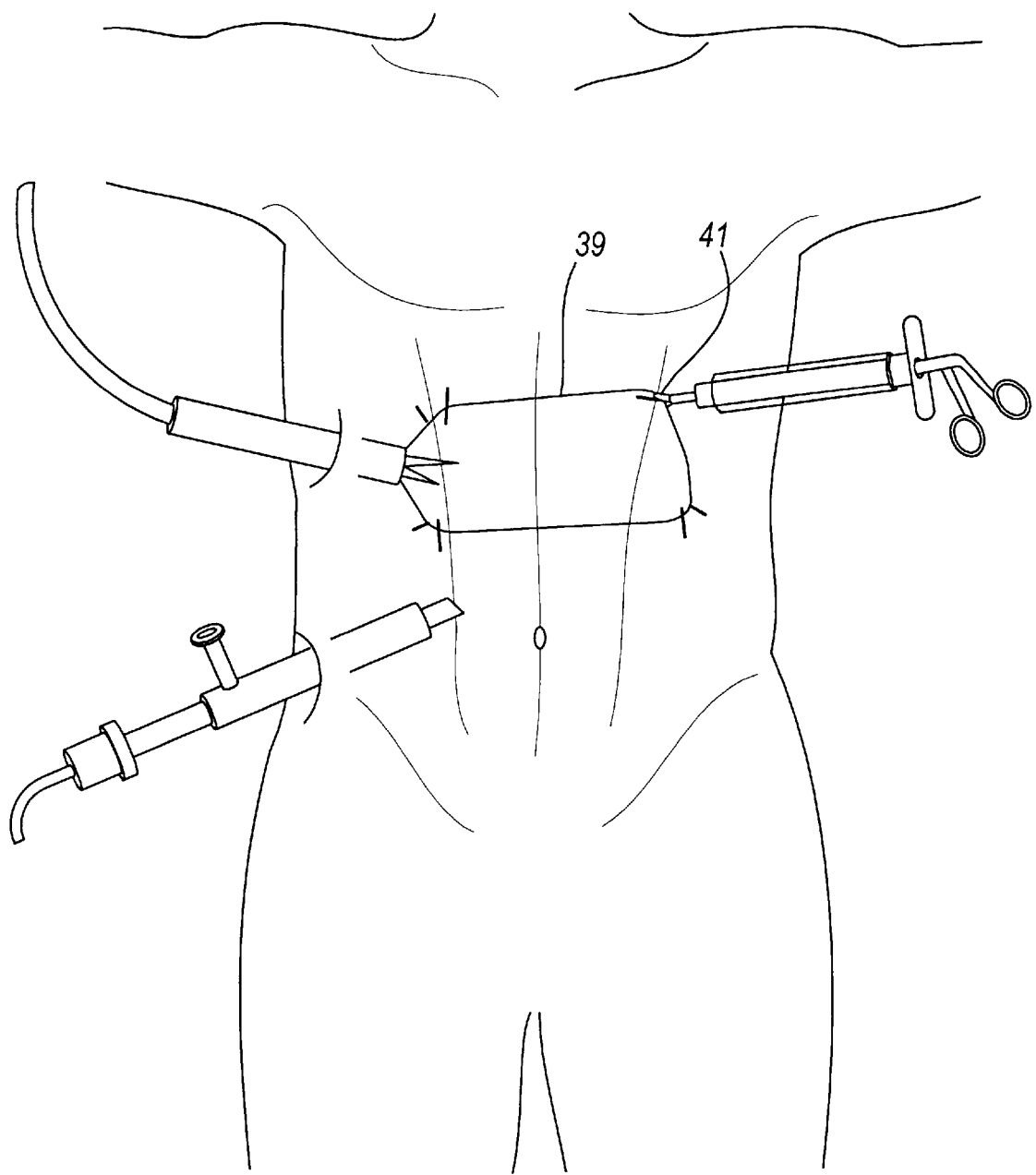
FIG. 5 illustrates how the device is positioned beneath the targeted fat using the forceps inserted through the patient's left side using surgical clips.

FIG. 5 illustrates the final positioning of the device (39) and its fixation to the underlying fascia with endoscopically placed staples (41).

Figure 6:
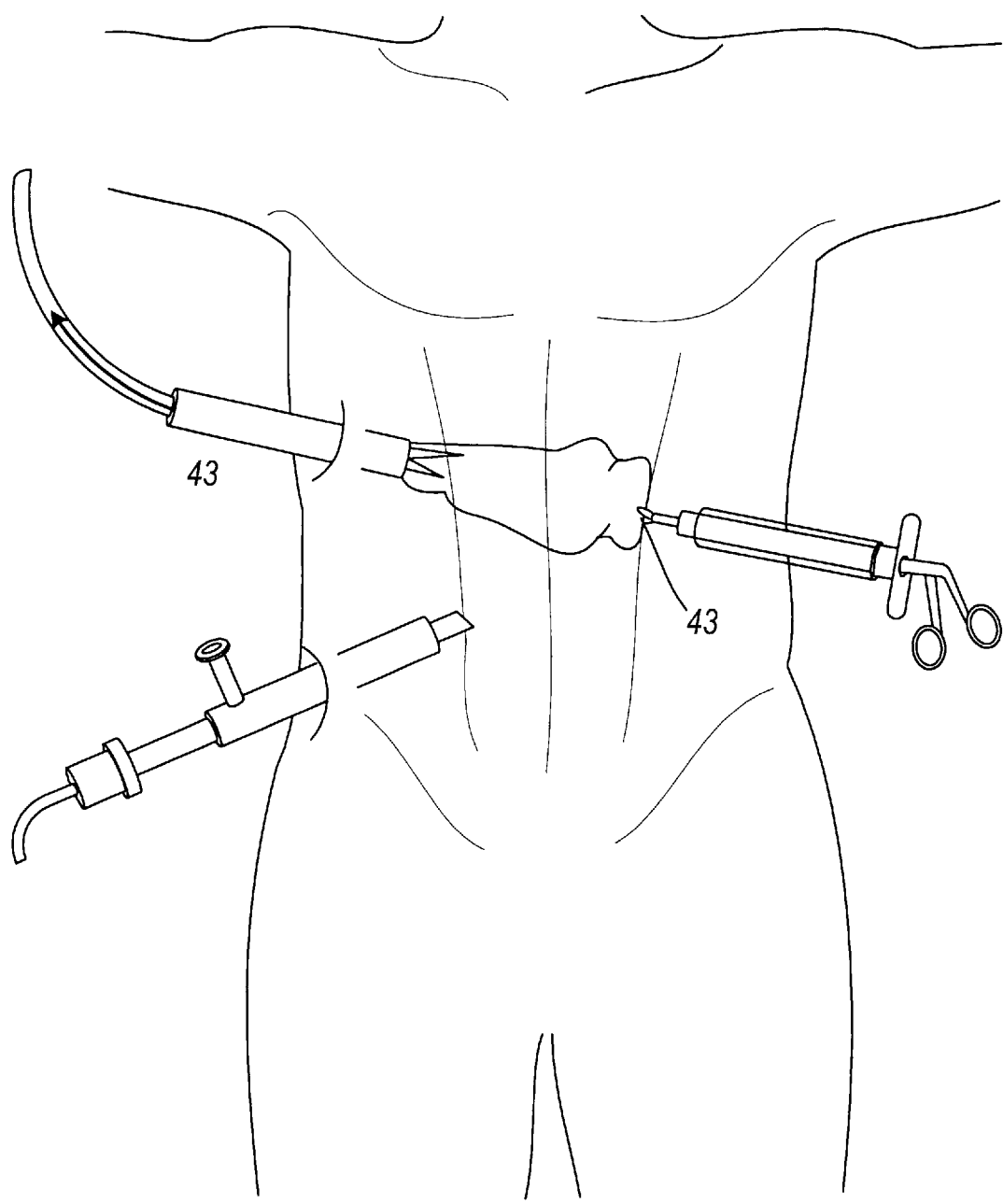
FIG. 6 illustrates how the device is removed from the body when a sufficient amount of fat has been destroyed.

When the desired amount of fat has been destroyed by induced apoptosis, the device is extracted from the body after release of the staples by a combination of traction (43) and assistance when necessary with a forceps placed through the left upper quadrant port, as illustrated in FIG. 6.

Figure 7:
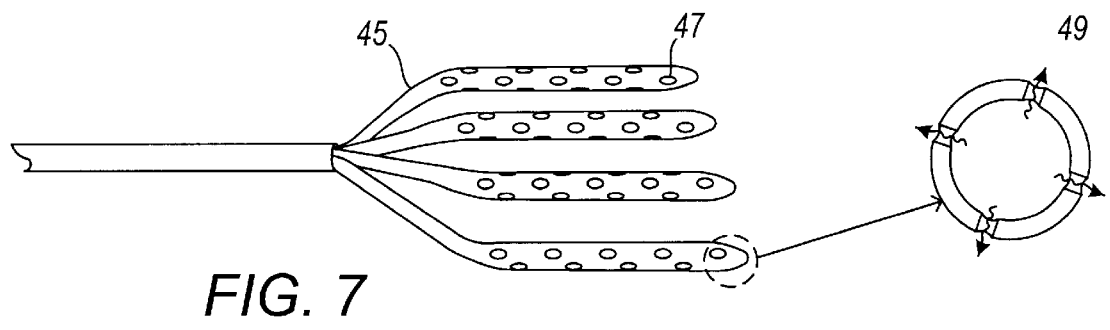
FIG. 7 indicates the configuration of the plastic delivery tubes that spread the soluble stimulants to trigger fat apoptosis over a broad area of adjacent fat in which they are in direct contact.

FIG. 7 illustrates how the delivery tubes (45) containing the soluble chemical apoptotic stimulating solutions are variously configured to spread their contents over the wide surface of the targeted fat. The tubes emerge from the endoscope in a bundle at the target site but their ends and delivery openings are spread diffusely over the area of targeted fat. This is achieved by the use of diffusely porous delivery tubes or those with side holes for delivery (47).

Figure 8:
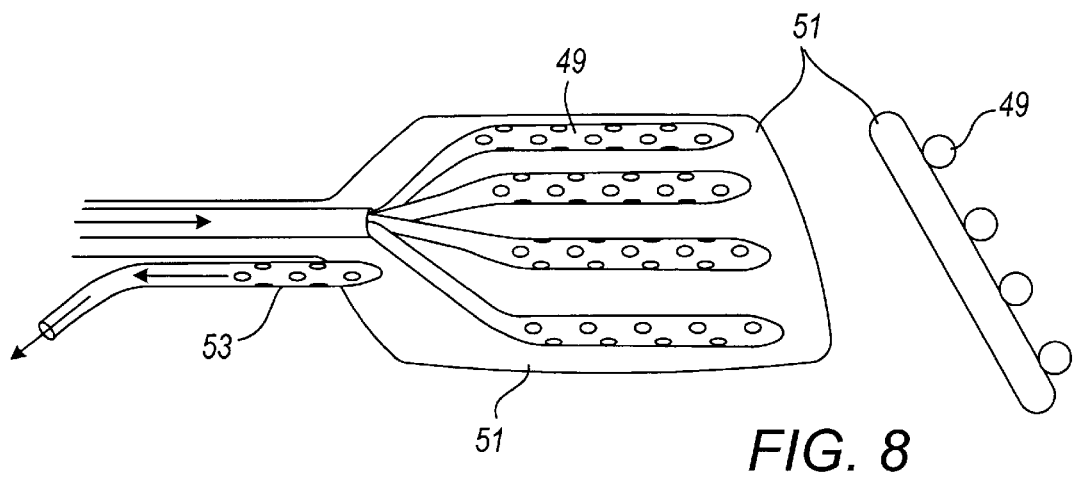
FIG. 8 illustrates how the delivery tubes are mounted on a broad, biologically inactive pad or skirt that serves to anchor the tubes and to protect the underlying fascia and fat.

FIG. 8 illustrates how the delivery tubes (49) are mounted on top of the broad base "skirt" (51) which keeps the solution primarily in contact with the targeted fat. It thus helps to minimize exposure of the stimulants to the tough underlying fascia to which the device is fixed. A suction catheter (53) at the base of the skirt removes the fat contents of the dead cells which slough off from the overlying fat.

Figure 9:
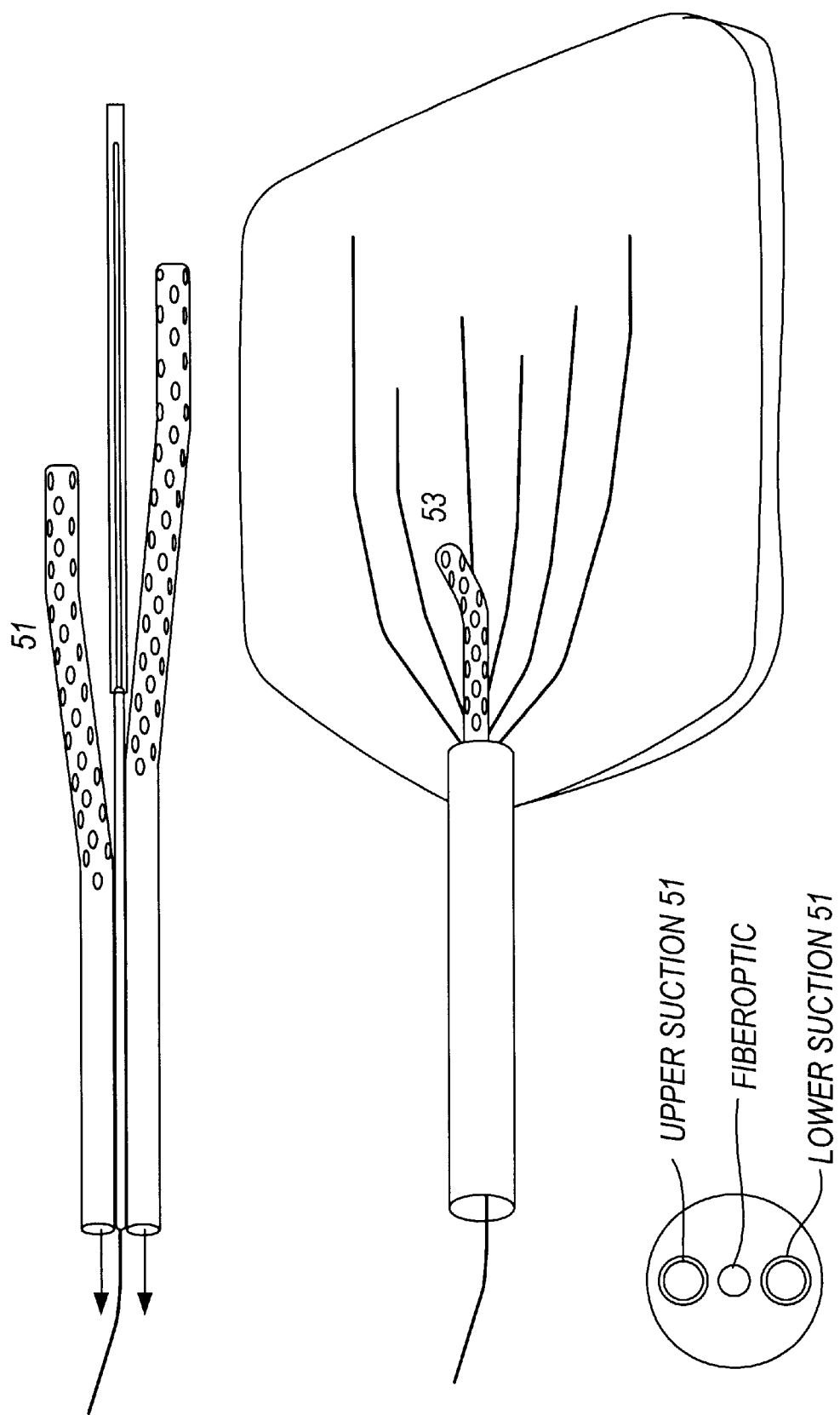
FIG. 9 illustrates how suction catheters above and below the delivery tubes remove the irrigating fluid, free fat, debris and remnants of the apoptotic fat cells.

FIG. 9 illustrates how several suction catheters (53) can be placed above and below the plastic base on which the delivery tubes are fixed. This Figure also indicates how varying lengths of delivery tubes spread the solution beneath the entire area of fat intended for self destruction.

Figure 10:
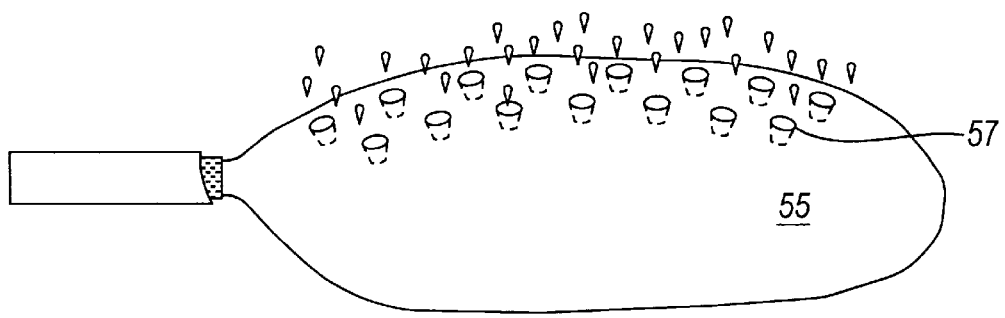
FIG. 10 illustrates how a solution of fat apoptosis stimulants can be delivered from a solution filled balloon. The upper portion of the balloon, which is permeable to the solution, continuously bathes the fat in an apoptotic stimulating environment.

Storage reservoirs for the solutions containing apoptotic stimulants can be of three types. As shown in FIG. 10, the solution can be stored beneath the fat in a distended balloon (55) the upper surface of which is made semipermeable (57) so that it slowly leaks the contained fluid from the balloon reservoir on to the superimposed fat. The pore size of the balloon can be constructed so there is a predictable rate of leakage.

Figure 11:
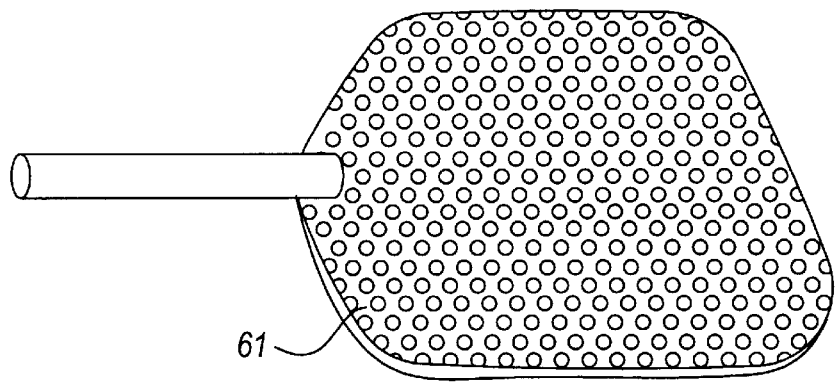
FIG. 11 illustrates how molecules of apoptosis stimulants can be loosely bonded to a mesh to be inserted in a space beneath fat, thus providing a slow release mechanism of the apoptotic stimulant.
Figure 11:
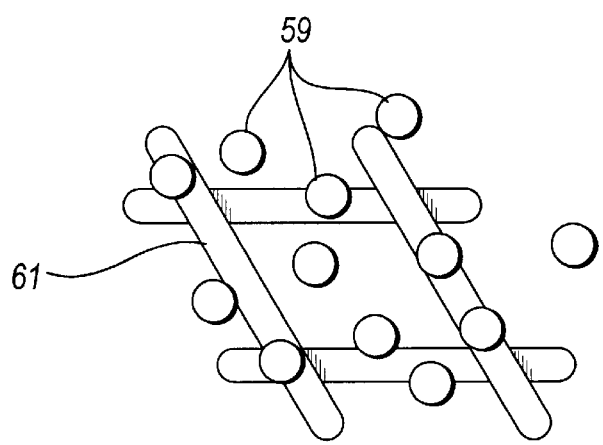

A second technique shown in FIG. 11 loosely bonds molecules of the apoptosis signals (59) to a plastic mesh (61) configured to release the chemicals at a predetermined rate. Such a slow molecule release technique is used for antibiotics in certain commercially available plastic mesh employed for repair of hernia.

Figure 12:
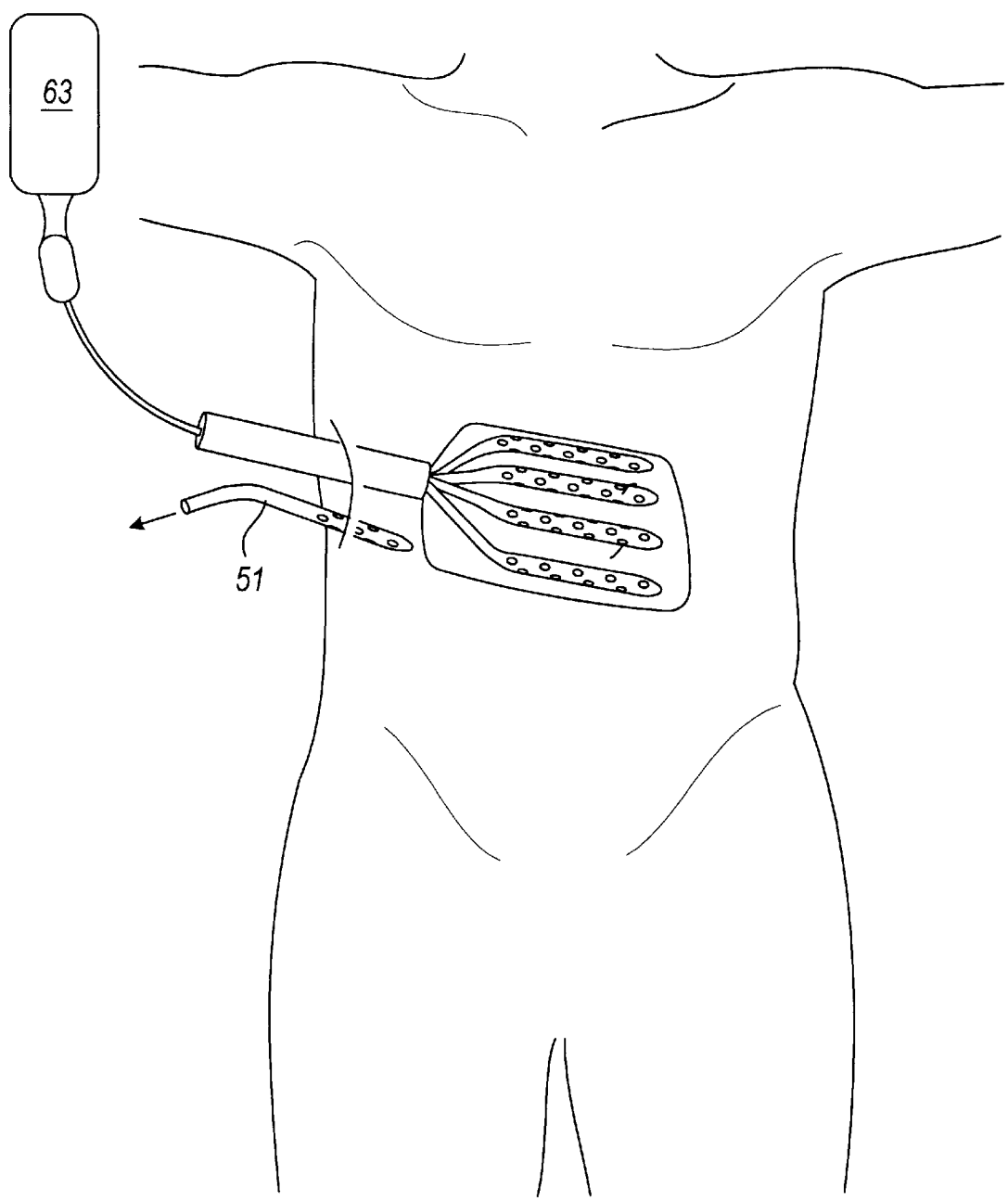
FIGS. 12 illustrates an overview of the irrigating system in place with a bottle of apoptotic solution stimulants dripping into the subcutaneous space by gravity drip and where a suction catheter at the base of the device removes the cell debris.

The third delivery system shown in FIG. 12 uses either a bottle (63) or bag as a reservoir, hung beside the patient. Flow from the reservoir into the subcutaneous space on to the fat is by gravity through a standard drip system. This technique is convenient for intermittent pulsed introduction of soluble fat apoptotic stimulants over a period of several days or weeks. Although this and other figures provide access to anterior abdominal wall fat depots, equivalent systems can be used elsewhere in the body where there is unwanted excess fat.

Figure 13A:
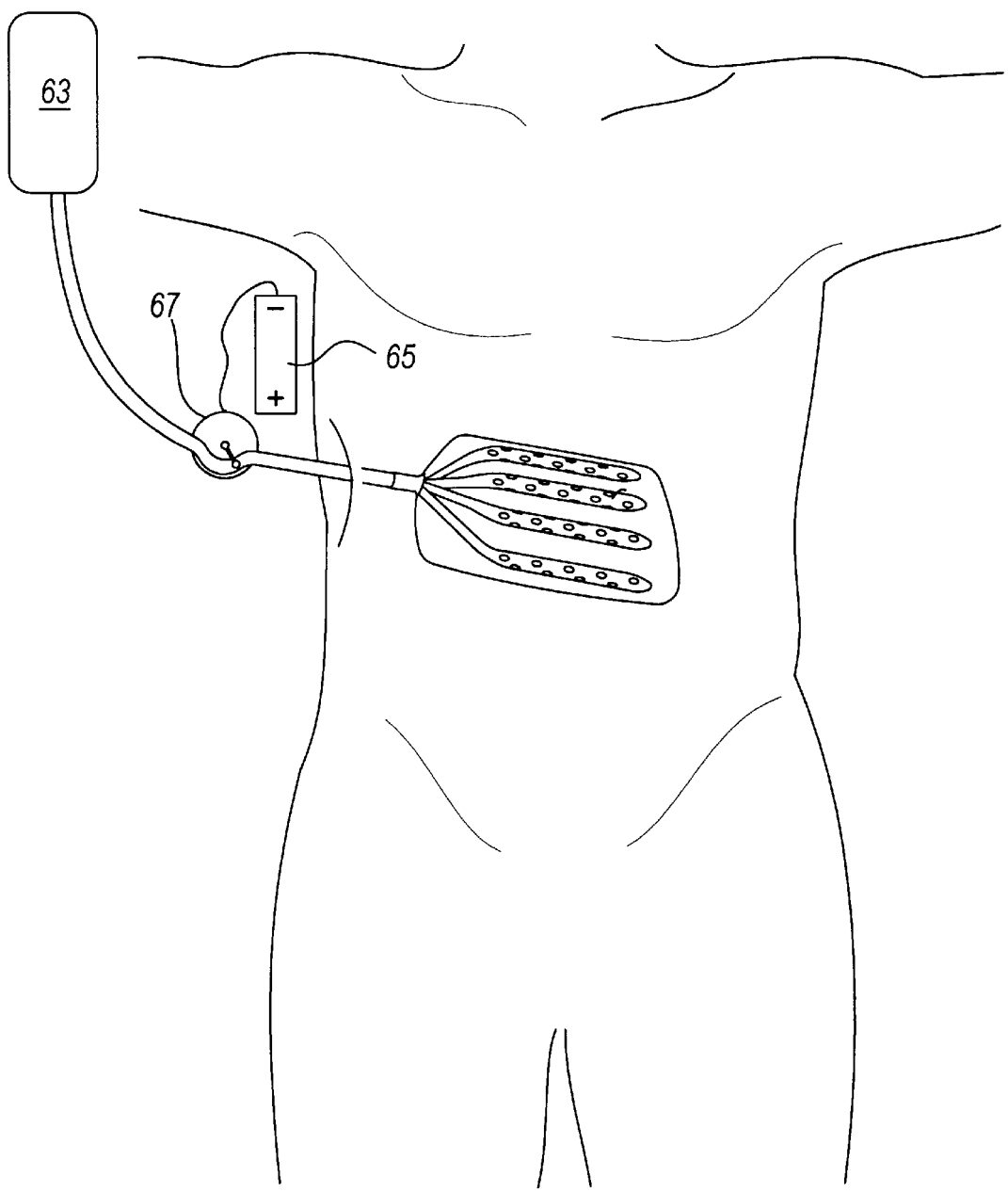
FIG. 13A is an overview of the embodiment of FIG. 11, but with the extracorporeal reservoir strapped to the chest wall and an electric battery powered pump slowly introducing the solution into the space beneath the fat, thus permitting continuous introduction of the soluble apoptosis stimulants over a period of several days or weeks.

FIG. 13A illustrates a system for chronic prolonged delivery of small volumes of the apoptotic stimulant solution. The fluid extracorporeal reservoir is a (63) strapped to the patient's thorax. A standard solution delivery tube (45) leads to a battery driven (65) roller pump (67) which infuses the solution into the porous delivery tubes in contact with the targeted fat depots. Such a system has been developed for delivery of insulin into certain patients with diabetes mellitus.

Figure 13B:
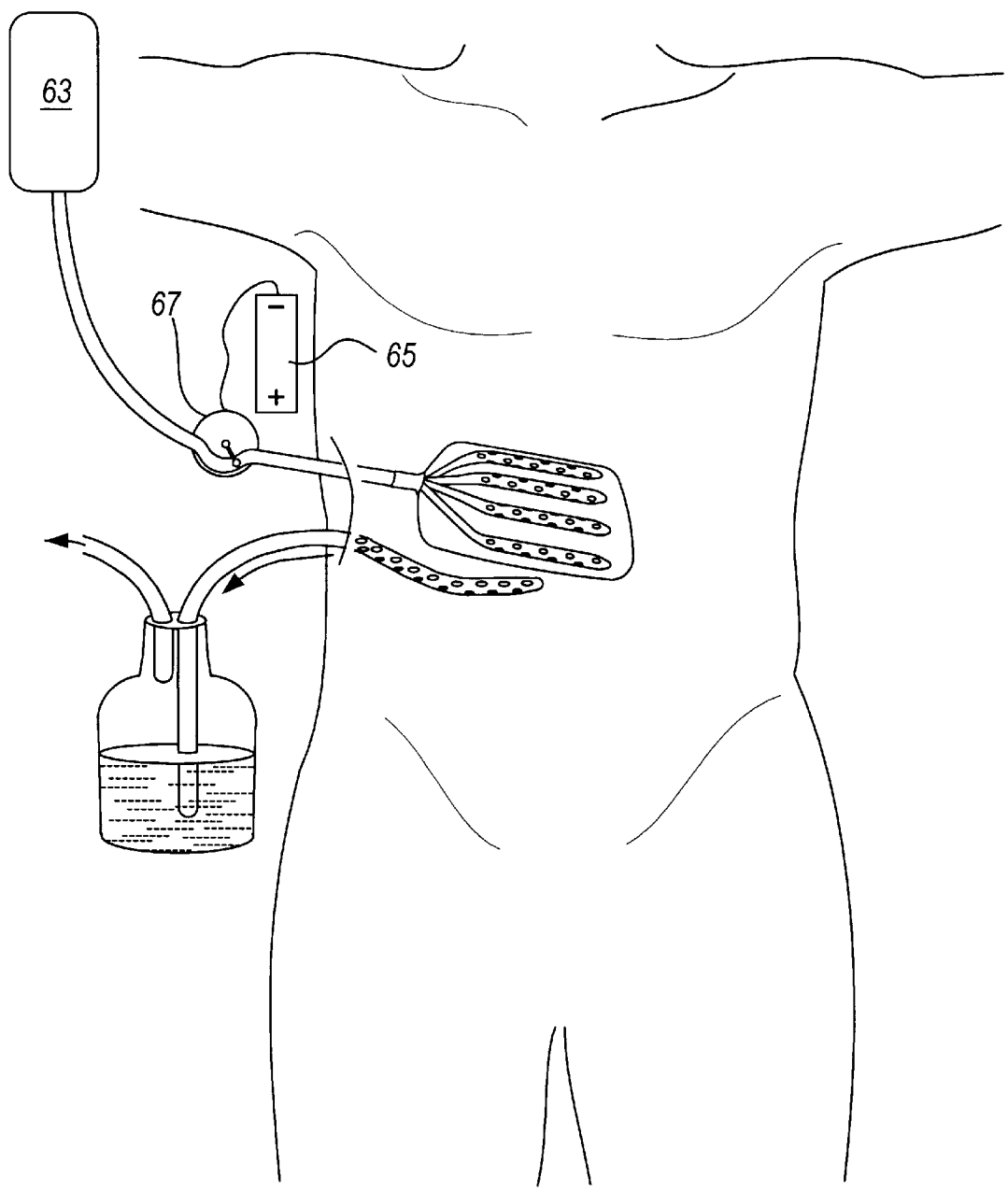
FIG. 13B illustrates the low pressure suction system for removal of free fat from the area of fat cell destruction by chemically stimulated apoptosis.

FIG. 13B illustrates the catheter suction system for removal of cell debris, and free fat released from disintegrated cells. The suction catheter (53) drains into a low pressure suction drainage bottle (69) as used in thoracostomy tube drainage. Removal of the debris from the site of fat cell apoptotic breakup, debrides the area and exposes new fat cells targeted for stimulation to undergo self destruction. This increases the efficiency of the fat removal process.

As previously described, the present inventor has recognized that ultra violet light (UV) stimulates apoptosis in certain types of lymphocytes by altering the nuclear. UV wave lengths of about 308 nm can be generated by various means and transmitted by special fiberoptics through small diameter fibers.

Figure 14:
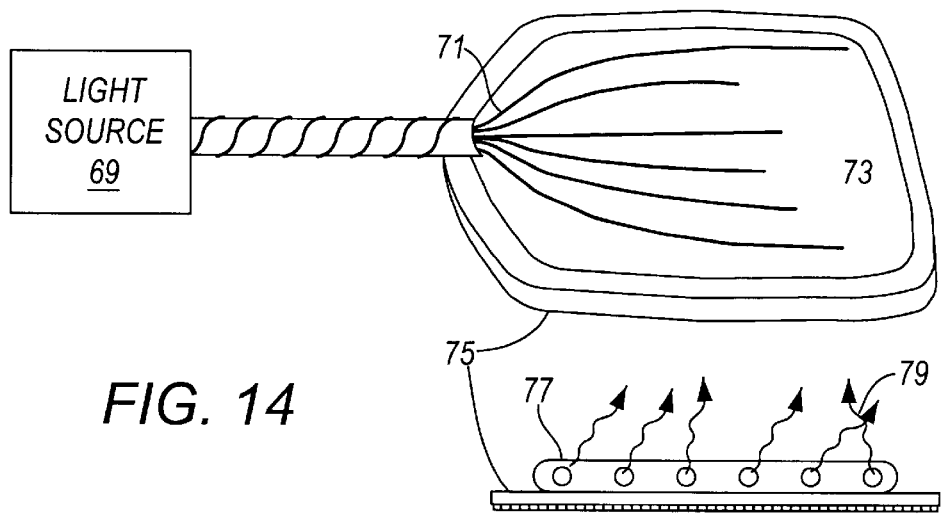
FIG. 14 is a diagrammatic representation of fiberoptics carrying Ultra Violet, or light of other wave length, from an extracorporeal source to fibers deployed to spread the light over a maximum area of subcutaneous fat, such fibers lying on a base or skirt that is impermeable to the light so that the underlying fascia and muscle are protected.

FIG. 14 illustrates the basic design of an embodiment for delivering UV (or other wave length light) from a source outside the body and its transmission by fiberoptics directly onto fat underneath the skin destined for destruction. The light generator (719) can be a free standing unit that produces UV (or other wave length light) at low power levels. The light is transmitted from the generator into the body beneath the skin by fiberoptics (73) which are configured by their differing length to spread the light source uniformly beneath the fat identified for self destruction. The terminal end of the fibers are embedded on a plastic sheet (75) configured to the targeted area for fat destruction. It is made of plastic impermeable to UV light to protect the underlying fascia and muscle. The top surface of the sheet (77) is made reflective to UV light, thus concentrating the reflected emitted light (79) on to the overlying unwanted fat.

Figure 15A:
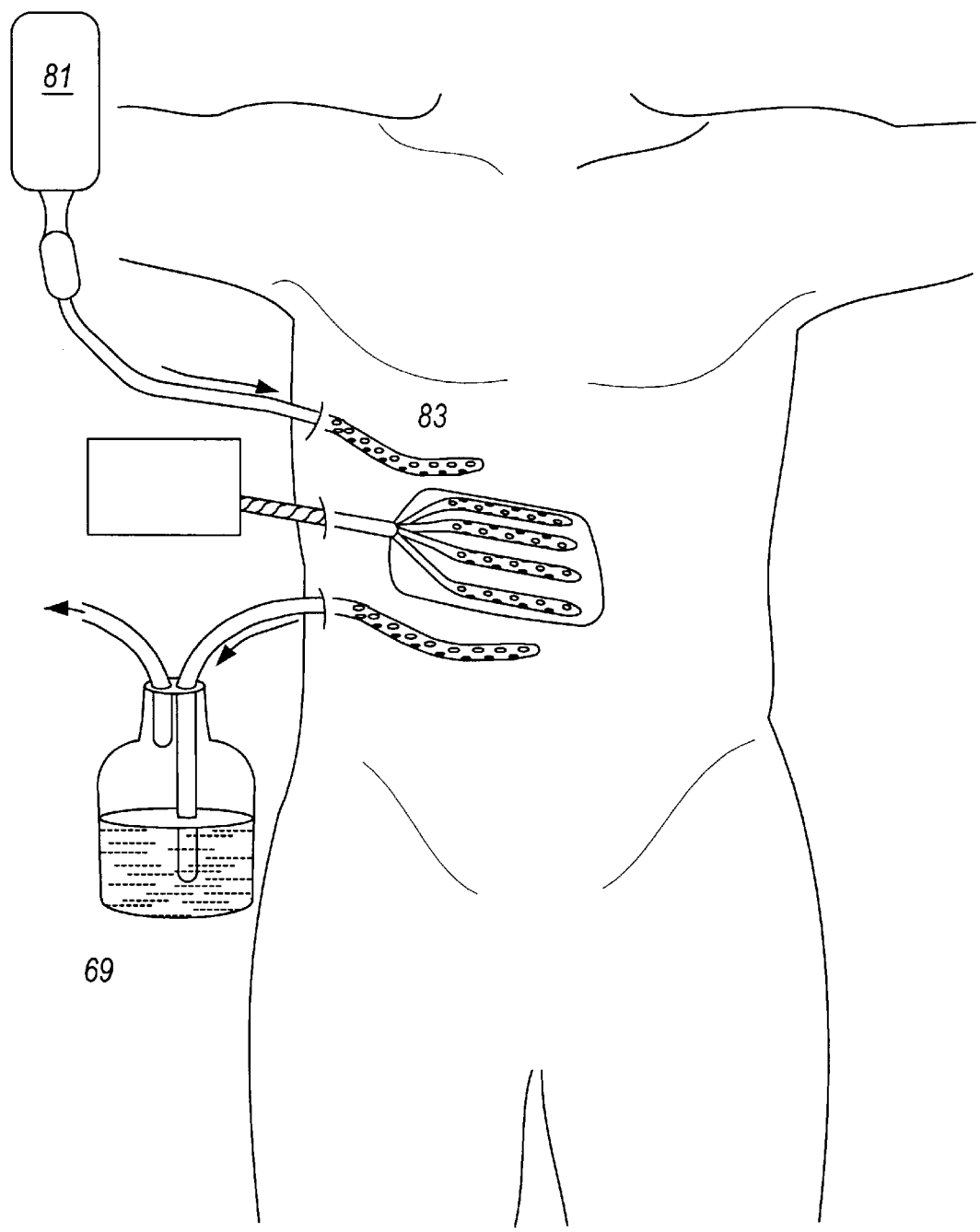
FIG. 15A illustrates how in flow and out flow catheters are used to debride the area of destroyed fat cells and free floating fat following exposure to UV.
Figure 15B:
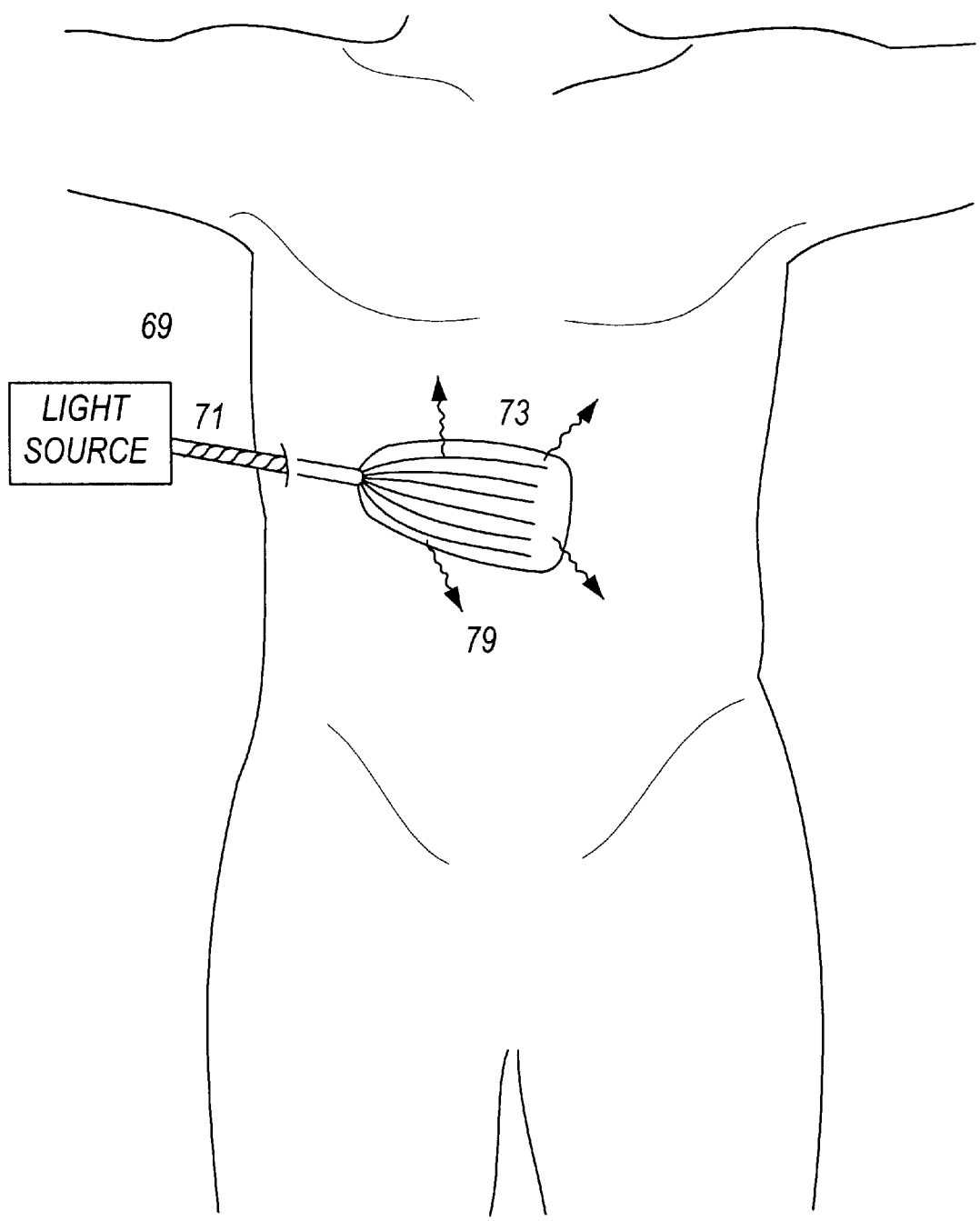
FIG. 15B illustrates how the fiberoptic system illustrated in FIG. 14 takes light emitted from a source outside the body and transmits it via fiberoptics to the targeted fat beneath the skin.

FIG. 15 illustrates how the invention is used clinically for inducing apoptosis in fat beneath the skin on the anterior abdominal wall. The light source (69) outside the body, transmits UV through the fiberoptics (71) to the displayed fibers (73) which direct the UV (79) on to the targeted fat.

In contrast to the system illustrated in FIG. 13 where the apoptotic signal is a chemical in solution, the UV signal as illustrated in FIG. 15 obviously is transmitted in a dry environment beneath the fat. In order to obtain the benefits of debridement and removal of destroyed fat cell elements, an irrigating system is used as illustrated in FIG. 15. An aqueous irrigating solution is stored in an extracorporeal reservoir (81). This can be a bottle or a bag. When low intensity UV stimulation is used over prolonged periods of days or weeks, a collapsible bag reservoir can be strapped to the chest wall, and the irrigating solution delivered through a multi-holed catheter (83) at a constant low flow.

Figure 16:
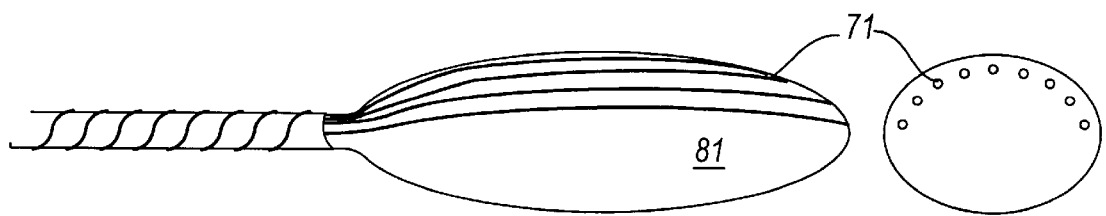
FIG. 16 diagrammatically illustrates how fiberoptics can be deployed on the top layer of a balloon which holds fibers in contact with the overlying fat, at the same time as it shields the underlying fascia and muscle from radiations.

FIG. 16 illustrates how the fibers emitting UV can be mounted on the superior surface of a balloon (81) which can be distended with water when the fibers are emitting UV light. The water filled distended balloon helps shield the underlying tissues from UV exposure.

Figure 17:
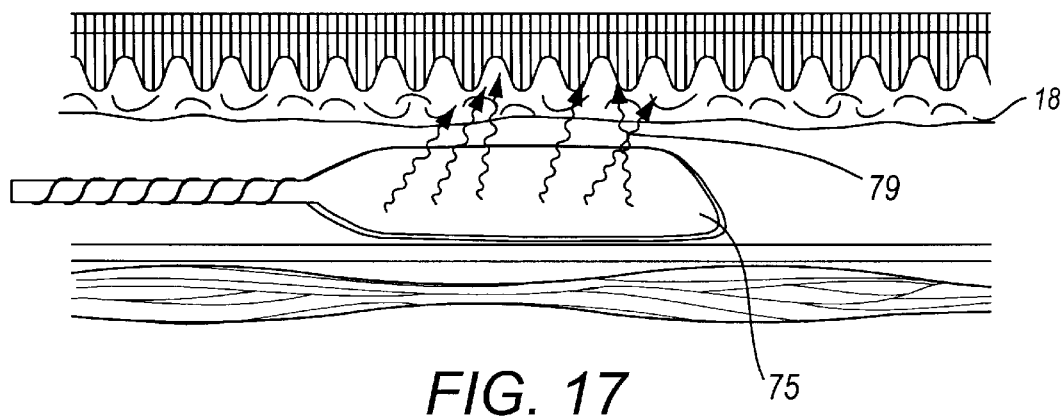
FIG. 17 illustrates how the effect of UV or red light exposure can be enhanced by staining the fat with a photodynamic dye.

FIG. 17 illustrates a method for increasing the absorptive capacity of UV light by the fat using proven techniques involving so called photodynamic dyes. Dyes (83), such as Sorlans, when taken by mouth are differentially absorbed and held temporarily in fat. They have the additional property of absorbing UV and certain other wave length light. As such they are used clinically in certain types of laser therapy. In the illustration of the balloon (75), the reflected UV light (79) and the photodynamic dye (83) tinting the fat (85) are used to induce apoptosis.

Figure 18:
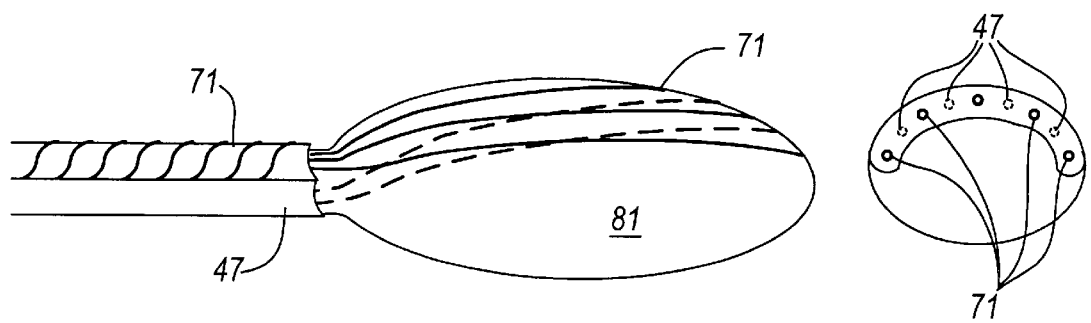
FIG. 18 diagrammatically illustrates how fiberoptics delivering light and tubes containing soluble fat apoptosis stimulants can be used simultaneously.

FIG. 18 illustrates how the two types of fat cell stimulants to produce apoptosis can be used simultaneously by clustering the two types of delivery tubes and fibers. Permeable delivery tubes delivering solutions of apoptosis stimulants (47) are interspersed between fibers delivering UV (71). In the illustration the fibers are deployed on the top of a distensible balloon (81). Because the two types of apoptosis stimulants function by different physiologic intracellular mechanisms, the two different types of stimulants have a potential for functional synergy.

Figure 19:
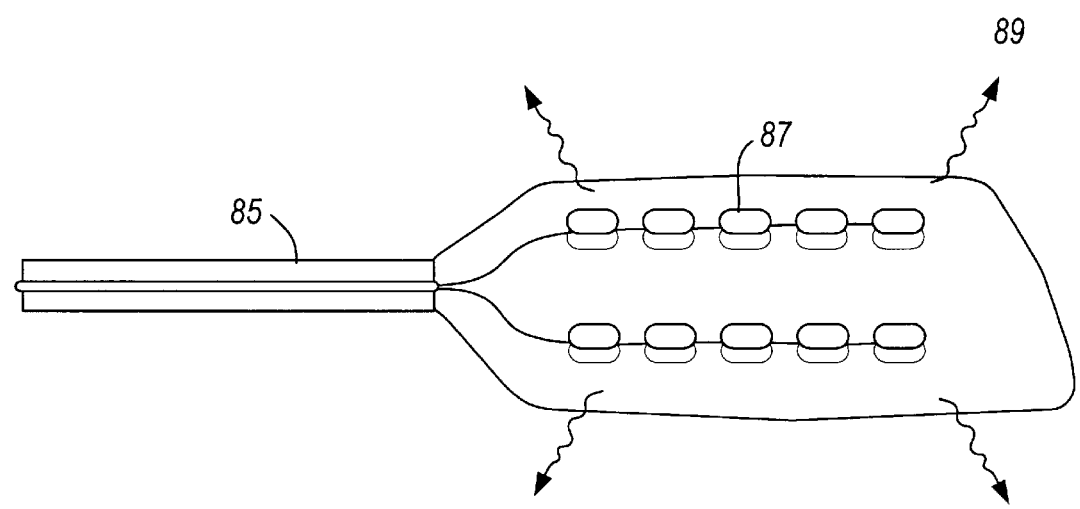
FIG. 19 illustrates a Light Emitting Diode (LED) which uses minute amounts of electricity to stimulate light from a crystal that can be implanted beneath the targeted fat.

In other embodiments, Infra red or light of wave lengths outside the UV range may be of clinical importance in causing fat destruction by apoptosis without simultaneously causing unwanted necrosis. A beneficial ratio of apoptosis to necrosis can be achieved using red or Infra red light delivered to the undersurface of targeted fat as illustrated in FIG. 19 and FIG. 20 using light emitting diodes.

Light emitting diodes (LED) using minute amounts of electricity are widely used for the white or red light which is familiar as signals on computers, dashboards of automobiles, coffee makers, or to illuminate the crystals of wrist watches. In FIG. 19 the wire leads (87) from an extracorporeal battery source to the series of LED's (89) displayed on a plastic pad. Red light (91) is illustrated as being emitted from the LED'S connecting the implanted series of LED (89).

Figure 20:
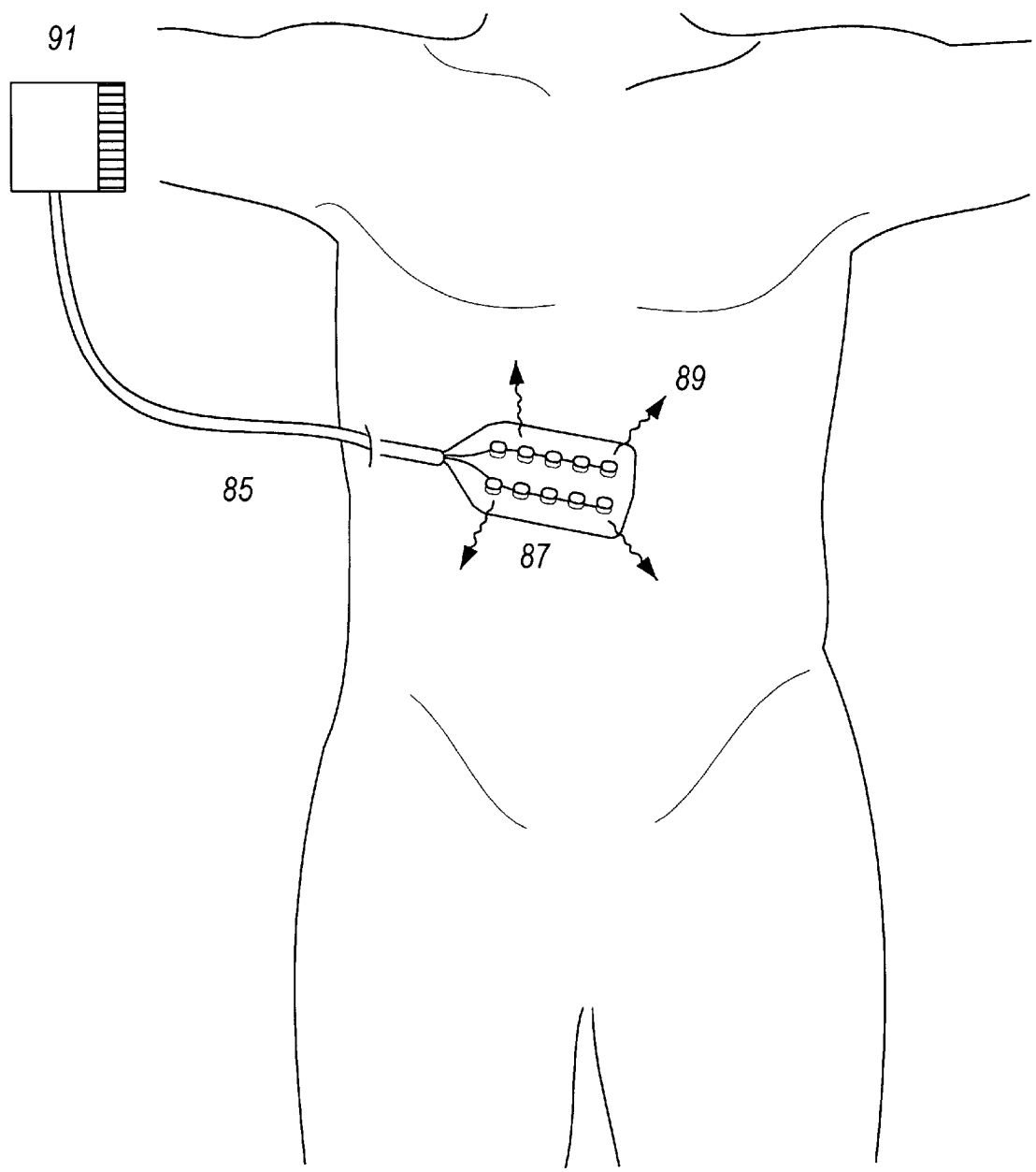
FIG. 20 is an array of diodes (LED'S) that can be used to emit light onto the inner surface of targeted fat.

FIG. 20 illustrates how the LED system can be used clinically. The extracorporeal battery source of low voltage electricity (93) is connected to the LED (89) by a small diameter wire (87). The LED's emit the light (89) directly beneath the targeted fat.

EXAMPLES

The following examples are illustrative only of particular embodiments of the present invention.

An experiment was performed to prove that fat cells could be stimulated to undergo apoptosis. Mouse fat cells (adipocytes) were grown in tissue culture and were exposed to stimulants 24 hours prior to fixation and quantitation of apoptosis using Hoechst stain. Apoptosis index was increased up to twenty percent (20%) above controls using three stimulants (i.e., dexamethasone, tumor necrosis factor and ultraviolet light) known to produce apoptosis in other cells. Beta UV (wavelength) approximately 300 nm to 305 nm. 50 m Joules$^2$ was directed onto the fat cells in culture. All of the fat cells, in contrast to the control cells, experience apoptosis events.

A determination was made as to the most efficient wavelength of UV light that produced apoptosis and that was least likely to provoke necrosis. A number of live cells, necrotic cells and cells in apoptosis were quantitated using various wavelengths of UV light. Approximately 300 nm was determined to be the most efficient wavelength for producing maximum apoptosis at minimum necrosis.

Animal studies were also performed using anesthetized mice. The fat deposits in the lower abdominal and inguinal region were surgically exposed so no protective skin overlaid the targeted fat cells. A UV light source at 305 nm was directed onto the fat for 12 seconds, delivering loom Joules/cm$^2$. The animals were sacrificed in 24 hours and the targeted fat fixed and studied for evidence of apoptosis and necrosis. A diffuse production of apoptosis in the specimens was observed and fat from destroyed cells was clearly evidenced.

Rat 3T3L1 adipocytes were prepared as follows: Fibroblasts were cultured in DMEN Media (Eagle Media plus dextrose to which 10% fetal calf serum was added 400 mica/ml gentamycin and 1 ngm glutamine). The cells were incubated at 37C for 5–6 days until confluent.

The medium was removed and differentiating medium added. This consisted of DMEN medium as above, plus isobutyl methyl xanthine (IBMX). After 48 hours this was converted to Adipocyte Growth medium by adding insulin which was changed every 2 days. By 10–12 days the fat cells had differentiated at which time serum was removed (serum starved) for 24 hours to get rid of insulin.

One group of fat cells were used in serum free medium, the other in the presence of serum. The controls grew simultaneously with the fat cells to which apoptosis stimuli had been added. Dexamethasone Decadron 0.25 mgm was added for 18 hours. Tumor Necrosis Factor (TNF alpha) was left on the cells for 4 hours. TNF plus Dexamethsome was left 4 hours. A total of 12 tubes were studied in the first studies. The suspended cells were washed, fixed and stained with Hoechst stain. Apoptosis was counted in a minimum of 1,000 cells under a fluorescent microscope by a trained technician. Triplicate studies were performed on each tube of cells.

Cyclohexamide (protein synthesis inhibitor) was used in a second study and demonstrated apoptosis approximately the equivalent to UV treatments.

Studies where performed to make a comparison between living cells, necrotic cells and apoptotic cells, using a double dye (Ethidium bromide and acridine orange) to differentiate necrosis from apoptosis.

The results of these studies can be summarized as follows:

1) Each of the following agents induced apoptosis in fat cells in tissue culture: Dexamethsome; Tumor Necrosis Factor alpha; Cyclohexamide, Ultra Violet Light Beta (308 nm).

2) Increase of apoptosis by the agents varied between 3 and 54 times the controls. All numbers had statistical significance at a 5% or better level.

3) Dose of UV (303 nm) studies indicated that a UV dose of 300 mJ/cm 2 provided maximum differentiation between lower doses (which provided too little stimulus to undergo apoptosis) and higher doses (which resulted in too high a level of necrosis). This suggests a dose of about 300 mjoules/cm2 should preferably be used.

The proper dose of UBV was determined as follows. The light source was a Dr. Honeley Indaescent UV Lamp Model SOL-3. To calibrate the dose with each study, we used a UV Meter (International Light Model 1350 which measures both UVA and UVB). The dose delivered in the reported studies was 100 m Joules/cm2. This involved an exposure of 5–9 seconds at approximately 20 cm from the fat target. Conversion from Watts provided the data required to use a standard and repeatable UV dose, since the light source proved to have certain inconsistencies. The specimens of fat were fixed in paraffin and examined histologically after staining with Hoechst stain for apoptosis, and Hematoxyllin and Eosin for viability or necrosis. Those specimens exposed to UV—in contrast to controls—demonstrated diffuse evidence of fat from destroyed fat cells, as well as the presence of widespread apoptosis of still intact fat cells.

The above discussion of the invention is for purposes of illustration and description. It is not intended to limit the invention to the form disclosed herein. Consequently, variations and modifications commensurate with the above techniques, within the skill and knowledge of the relevant art, are within the scope of the present invention. The embodiments described hereinabove are further intended to explain the best mode presently known of practicing the invention and to enable others skilled in the art to utilize the invention as such, or in other embodiments, and with the various modifications required by the particular application or uses of the invention. It is intended that the appended claims be construed to include alternative embodiments to the extent permitted by the prior art.

What is claimed is:

1. A method to reduce the volume of adipose tissue, comprising contacting adipose tissue with an effective amount of an apoptotic inducing factor to cause apoptosis of said adipose tissue, wherein said apoptotic inducing factor is UV light.

2. A method to reduce the volume of adipose tissue, comprising contacting adipose tissue with an effective amount of an apoptotic inducing factor to cause apoptosis of said adipose tissue, wherein said apoptotic inducing factor is UV light, and wherein said UV light comprises primarily beta rather than alpha UV radiation.

3. A method to reduce the volume of adipose tissue, comprising contacting adipose tissue with an effective amount of an apoptotic inducing factor to cause apoptosis of said adipose tissue, wherein said apoptotic inducing factor comprises both UV light and a chemical substance.

4. A method to reduce the volume of adipose tissue, comprising contacting adipose tissue with an effective amount of an apoptotic inducing factor to cause apoptosis of said adipose tissue, wherein said apoptotic inducing factor is inserted into a patient's body by biologically inert, small diameter tubes for apoptotic chemicals and by biologically inert fiber optics for UV light.

5. A method to reduce the volume of adipose tissue, comprising contacting adipose tissue with an effective amount of an apoptotic inducing factor to cause apoptosis of said adipose tissue and delivering photo-dynamic dyes that absorb UV light and that are selectively absorbed by fat tissue.

* * * * *